United States Patent
Camprasse et al.

(10) Patent No.: US 10,932,916 B2
(45) Date of Patent: Mar. 2, 2021

(54) METHOD FOR PRODUCING OSTEOSYNTHESIS DEVICES, OSTEOSYNTHESIS DEVICES AND IMPLANTS MADE OF SEMI-SYNTHETIC HYBRID MATERIAL OBTAINED BY STRUCTURAL MODIFICATION OF THE COMPONENTS OF A NATURAL MARINE BIOMATERIAL

(71) Applicant: MBP (MAURITIUS) LTD, Port Louis (MU)

(72) Inventors: Georges Camprasse, Arnage (FR); Serge Camprasse, La Fleche (FR)

(73) Assignee: MBP (MAURITIUS) LTD, Port Louis (MU)

(*) Notice: Subject to any disclaimer, the term of this patent is extended or adjusted under 35 U.S.C. 154(b) by 0 days.

(21) Appl. No.: 16/452,812

(22) Filed: Jun. 26, 2019

(65) Prior Publication Data
US 2019/0314165 A1 Oct. 17, 2019

Related U.S. Application Data

(62) Division of application No. 14/592,156, filed on Jan. 8, 2015, now Pat. No. 10,478,309.

(Continued)

(51) Int. Cl.
*A61F 2/44* (2006.01)
*A61B 17/80* (2006.01)
(Continued)

(52) U.S. Cl.
CPC .............. *A61F 2/442* (2013.01); *A61B 17/80* (2013.01); *A61B 17/86* (2013.01); *A61B 17/866* (2013.01);
(Continued)

(58) Field of Classification Search
CPC ....... A61B 17/80; A61B 17/86; A61B 17/866; A61B 17/72; A61C 8/0016; A61C 8/0074;
(Continued)

(56) References Cited

U.S. PATENT DOCUMENTS 4,769,040 A * 9/1988 Wevers ............... A61F 2/389
623/20.32
5,332,475 A 7/1994 Mechanic
(Continued)

FOREIGN PATENT DOCUMENTS

| FR | 0954066 A | 6/2009 |
|----|-----------|--------|
| FR | 2946888 A1 | 12/2010 |
| WO | 2010146308 A1 | 12/2010 |

OTHER PUBLICATIONS

Preliminary Search Report, dated Sep. 23, 2014, in corresponding French Patent Application No. 1450204.
(Continued)

*Primary Examiner* — Nicholas D Lucchesi
(74) *Attorney, Agent, or Firm* — Maier & Maier, PLLC

(57) ABSTRACT

A semi-synthetic hybrid material having a pH from 7 to 7.4 includes an inorganic fraction and a cross-linked organic fraction. The method for producing this material, and osteosynthesis devices or implants made of semi-synthetic hybrid material are also described.

5 Claims, 12 Drawing Sheets

Related U.S. Application Data

(60) Provisional application No. 61/925,753, filed on Jan. 10, 2014.

(51) Int. Cl.

| | | |
|---|---|---|
| *A61B 17/86* | (2006.01) | |
| *A61L 31/00* | (2006.01) | |
| *A61L 31/12* | (2006.01) | |
| *A61L 27/44* | (2006.01) | |
| *A61C 8/00* | (2006.01) | |
| *A61L 27/36* | (2006.01) | |
| *A61F 2/08* | (2006.01) | |
| *A61B 17/72* | (2006.01) | |
| *B29L 31/00* | (2006.01) | |
| *A61F 2/30* | (2006.01) | |
| *A61F 2/46* | (2006.01) | |
| *A61B 90/00* | (2016.01) | |

(52) U.S. Cl.
CPC .......... *A61C 8/008* (2013.01); *A61C 8/0016* (2013.01); *A61C 8/0074* (2013.01); *A61F 2/4455* (2013.01); *A61L 27/3604* (2013.01); *A61L 27/365* (2013.01); *A61L 27/446* (2013.01); *A61L 31/005* (2013.01); *A61L 31/128* (2013.01); *A61B 17/72* (2013.01); *A61B 17/8057* (2013.01); *A61B 17/8605* (2013.01); *A61B 2090/037* (2016.02); *A61F 2/0811* (2013.01); *A61F 2002/0817* (2013.01); *A61F 2002/30164* (2013.01); *A61F 2002/30261* (2013.01); *A61F 2002/30797* (2013.01); *A61F 2002/30971* (2013.01); *A61F 2002/4629* (2013.01); *A61F 2310/00347* (2013.01); *A61L 2430/02* (2013.01); *B29K 2995/0056* (2013.01); *B29L 2031/753* (2013.01); *Y10T 29/4998* (2015.01); *Y10T 29/49995* (2015.01)

(58) Field of Classification Search
CPC ... A61C 8/008; A61L 27/3604; A61L 27/365; A61L 31/005; A61L 31/128; A61L 27/446; A61F 2/446; A61F 2/4455; A61F 2/442
See application file for complete search history.

(56) References Cited

U.S. PATENT DOCUMENTS

| | | |
|---|---|---|
| 5,618,549 A | 4/1997 | Patat |
| 5,755,787 A | 5/1998 | Camprasse et al. |
| 5,768,134 A | 6/1998 | Swaelens et al. |
| 5,773,034 A | 6/1998 | Camprasse et al. |
| 6,093,530 A | 7/2000 | McIlroy et al. |
| 8,485,458 B2 | 7/2013 | Camprasse et al. |
| 8,636,236 B2 | 1/2014 | Zhi et al. |
| 2011/0004218 A1 | 1/2011 | Drai et al. |
| 2012/0207839 A1 | 8/2012 | Liu et al. |
| 2013/0310948 A1 | 11/2013 | Luscher et al. |
| 2015/0147397 A1 | 5/2015 | Altschuler |
| 2015/0374880 A1 | 12/2015 | Altschuler |

OTHER PUBLICATIONS

Chinese Office Action for Application No. 201580004180.3, dated Apr. 4, 2019.

Japanese Office Action for Application No. 2016-563268, dated Feb. 12, 2019 with English translation provided.

* cited by examiner

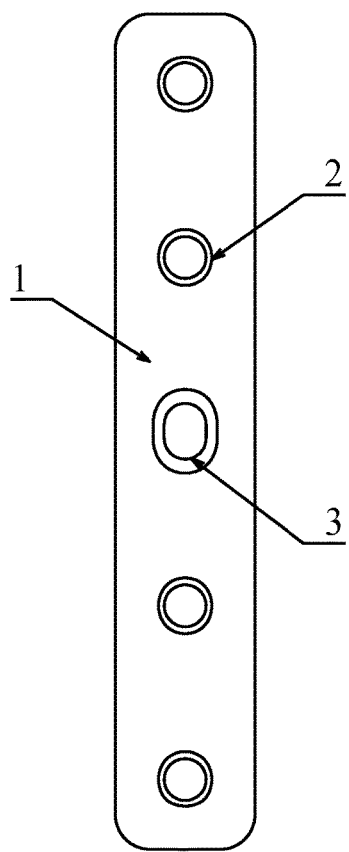 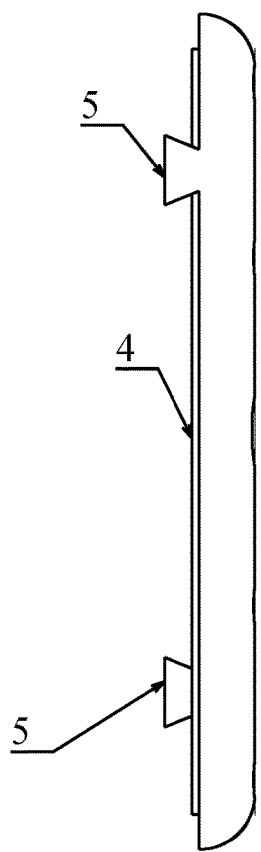 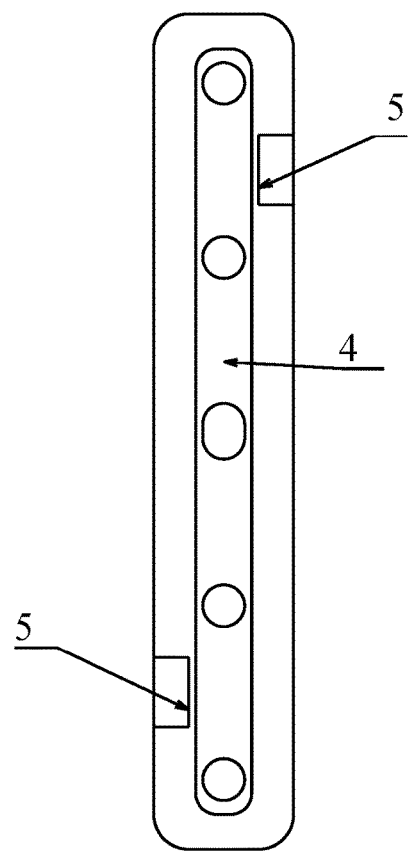
Figure 1a                    Figure 1b                    Figure 1c

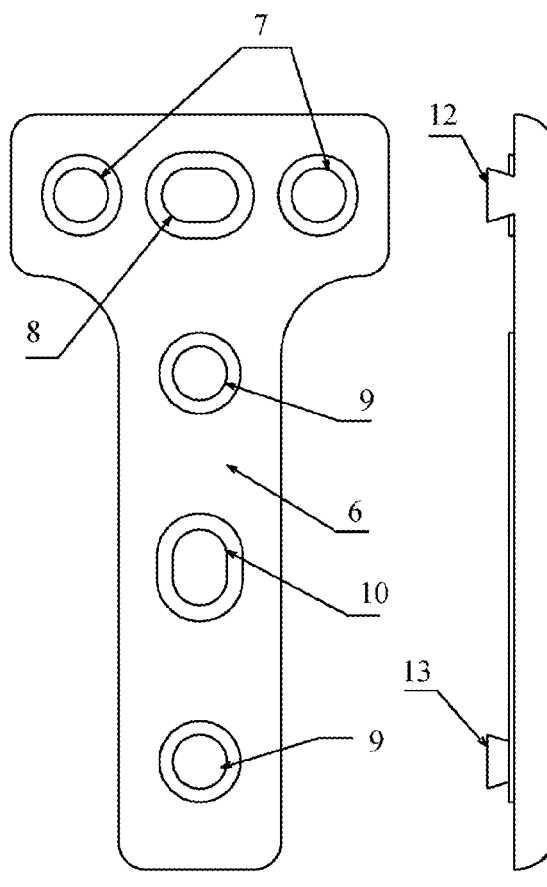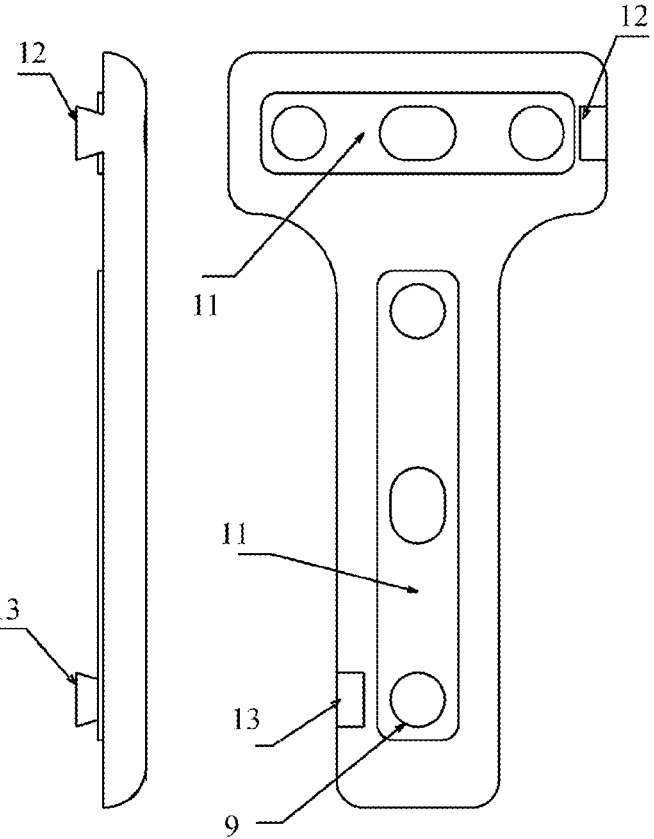
Figure 2a          Figure 2b          Figure 2c

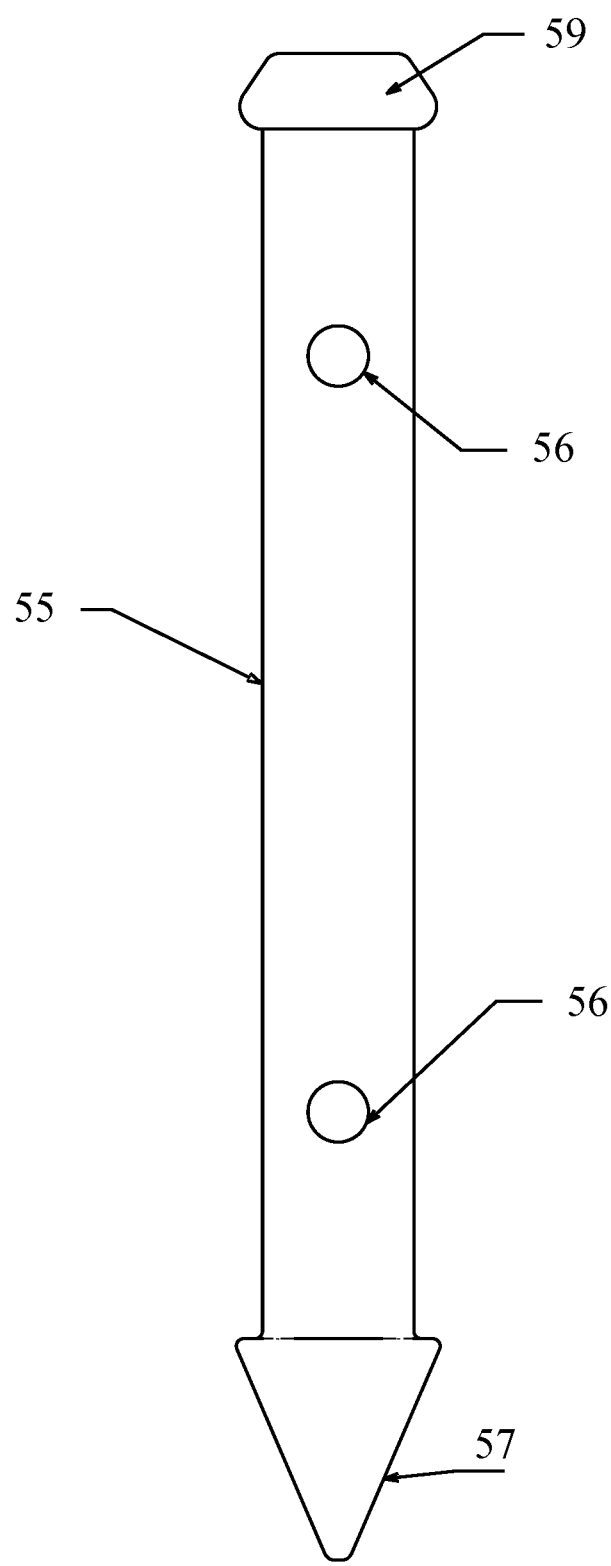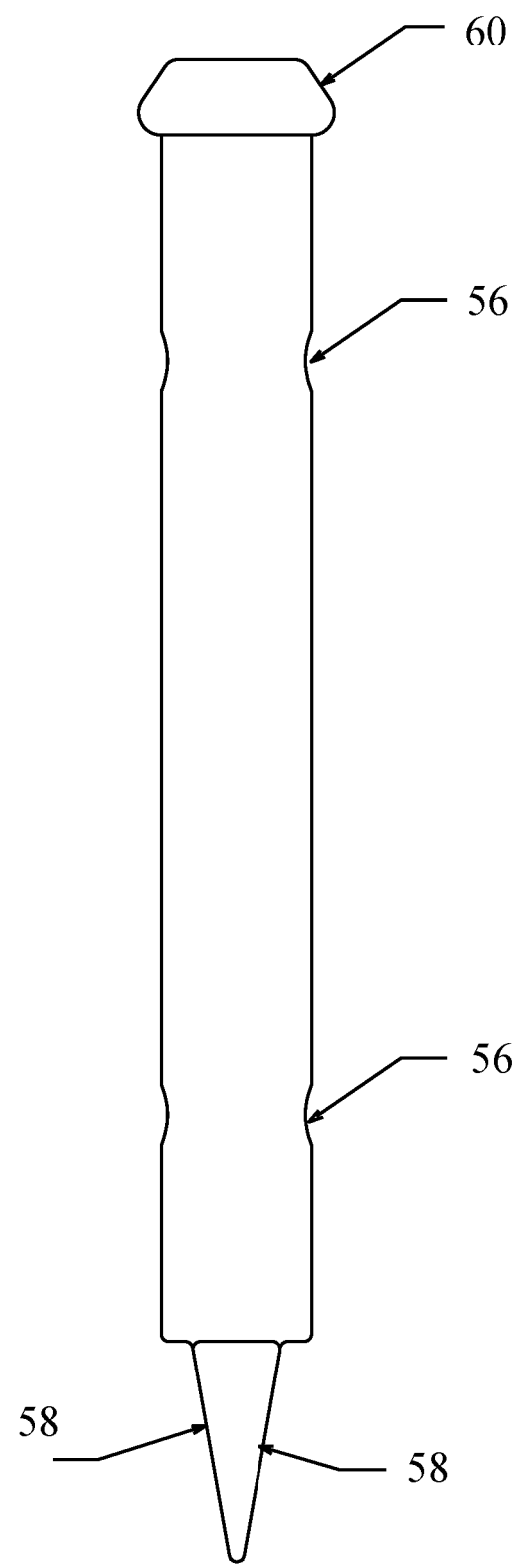
Figure 9a                    Figure 9b

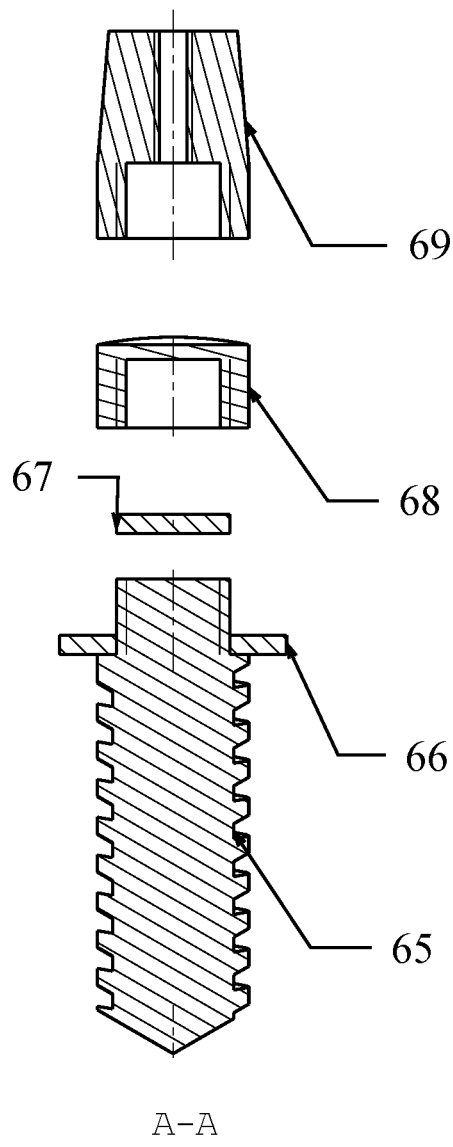
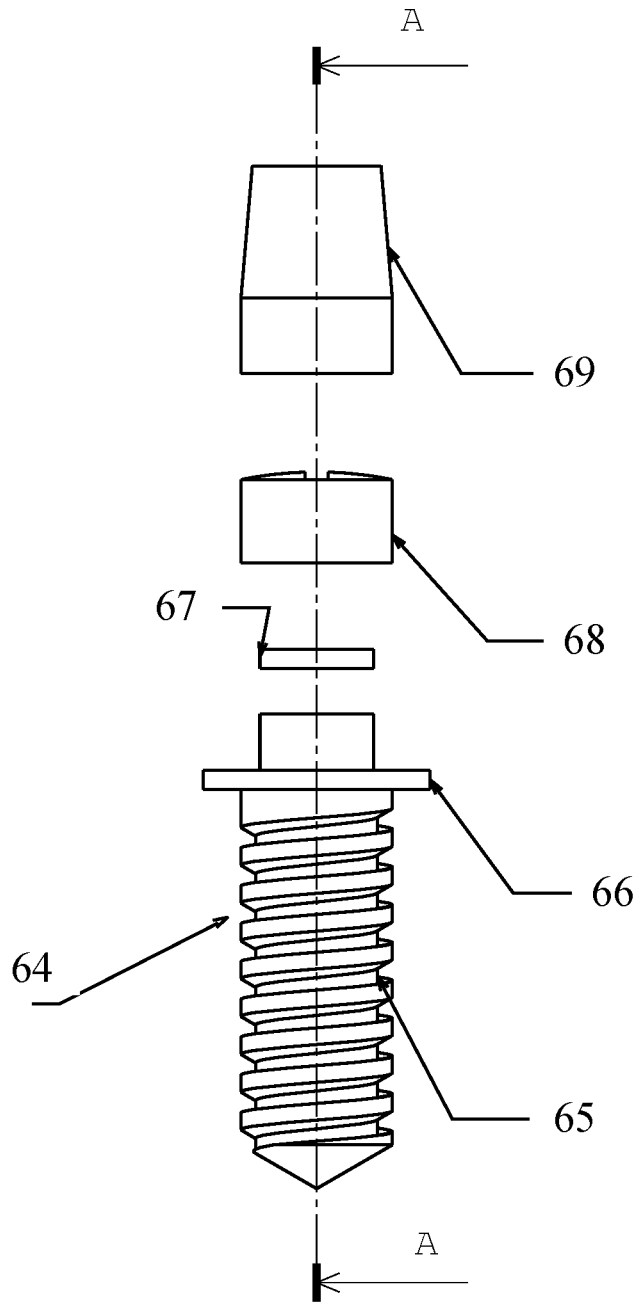
Figure 11a                    Figure 11b

METHOD FOR PRODUCING OSTEOSYNTHESIS DEVICES, OSTEOSYNTHESIS DEVICES AND IMPLANTS MADE OF SEMI-SYNTHETIC HYBRID MATERIAL OBTAINED BY STRUCTURAL MODIFICATION OF THE COMPONENTS OF A NATURAL MARINE BIOMATERIAL

CROSS-REFERENCE TO RELATED APPLICATIONS

This application is a divisional of U.S. patent application Ser. No. 14/592,156, filed Jan. 8, 2015, which claims benefit of U.S. Provisional Patent Application No. 61/925,753, filed Jan. 10, 2014, the entire contents of which are incorporated herein by reference.

FIELD OF THE INVENTION

The present invention relates to a semi-synthetic hybrid material obtained by structural modification of the components of a natural marine biomaterial, in particular the nacreous aragonitic layer of valve sea mollusks such as *Pinctada maxima, Pinctada margaritifera, Tridacnae maxima, Tridacnae gigas* and other *Pinctada* species. The present invention also relates to the production of osteosynthesis devices and implants from said semi-synthetic hybrid material.

BACKGROUND

The method most commonly used on fractures, apart from the reduction thereof by external ways, is osteosynthesis, which involves realigning the fractured segments by using plates, screws, nails and external fixators, made of stainless steel or of alloys of titanium, cobalt, etc., so as to immobilize the fractured fragments in order to permit the formation of a fibrocartilage callus.

The presence of the orthopedic material throughout the period of consolidation creates new mechanical and metabolic conditions since, on the one hand, the osteosynthesis material does not have the same mechanical and physical properties as the bone, especially Young's modulus, bending strength, elasticity, hardness, density and since, on the other hand, it suffers the corrosive action of the saline environment of the liquids circulating in the human body, which action releases metallic microparticles, ions, and various metal salts. This is followed by the appearance of inflammatory phenomena which may cause the formation of a fibrous envelope and may generate pain, edema, infection, fistulas, abscesses, bone resorption and sequestra at the periphery of the implant, which signs may appear several months after the implantation of the material. Thus, in some patients in whom the orthopedic material was implanted only 2 years previously, it has been possible to observe, in tissue samples taken from around the osteosynthesis material, a relatively high rate of metallic inclusions, chronic inflammation, oxidoreduction reactions, galvanic corrosion, fibrosis, metallosis or tissue necrosis, which is explained by a degradation of the plates and the release of toxic metallic ions such as cobalt, aluminum, etc.

In view of the metallic nature of the osteosynthesis material, an infection of the operating site may be difficult to treat generally, since the metal is impermeable by nature and thus opposes the diffusion of the therapeutic agent. It has also been possible to demonstrate that, during the bending of the plates in order to adapt them to the topography of the bone contour at the implantation site, this caused fissures and incipient breaks aggravated by the action of the circulating fluids and by the mechanical stresses, on account of the difference in the physical and chemical characteristics of the bone and of the metal. In addition, several months or even several years after the surgery, it is sometimes possible to observe a migration of the plates due to the mobilization of the fixing screws, since the tribology properties of the metal may be difficult to modify in view of its nature. Indeed, any modification of the surface state of the metal may make it vulnerable to corrosion and may alter its mechanical properties. In order to improve the tribology properties of the osteosynthesis material and of the metallic implants, they have been covered with a coating of hydroxyapatite by a sintering method using a plasma torch, in order to obtain the adhesion of metaplasic bone to the interface during healing of the bone. However, in most cases, the coating comes loose and fibrous tissue forms, which results in the mobilization of the osteosynthesis material or of the implants.

Originally, the osteosynthesis material was intended to be removed once the consolidation of the fracture had been confirmed clinically and radiologically. However, in a significant number of cases, the osteosynthesis material is left in place, since a new surgery in order to remove it would necessitate further hospitalization and an surgery almost identical to the first one, with the usual complications associated with any surgical intervention, a fortiori on bone. Indeed, the removal of the osteosynthesis material leaves a bone with drill holes and with a thinned cortex because of a lack of vascularization caused by the pressure of the plate. This results in secondary weakening of the operating site with the possibility of fracture.

Some cases require the urgent removal of the osteosynthesis material, for the following reasons: complaints by the patient, localized pain, prominence of the material, localized infections, pseudarthrosis, migration and fracturing of the material, bone fracture around the implant, toxicity and allergy.

Removal is also almost obligatory in the case of clavicle fractures requiring surgical management, because of the subcutaneous situation and the presence of vessels and nerves such as the brachial plexus and the subclavian artery, and the risk of pseudarthrosis resulting from the ischemia caused by the pressure of the plate on a flat bone.

Removal is also essential in pediatric orthopedic surgery, which does not obey the same rules as those in adult surgery; in particular, when the fracture involves the epiphyseal-diaphyseal region of a long bone, this region in the child encompasses the metaphysis, the site of the conjugation cartilage responsible for the growth of bone. The continued presence of osteosynthesis material at this level over a too long period of time will compromise the growth of the limb. These are the reasons why, in children, the orthopedic material is removed at an early stage so as to avoid this disadvantage. In doing so, one sometimes observes pseudarthroses and fractures which are caused by weakening of the bone, not to mention the complications associated with the removal of the material.

It is also known that, during the treatment of a fracture by osteosynthesis, the process of bone consolidation is modified. Indeed, when implanting plates and screws made of metal, alloy or any other material, it is necessary to evacuate the fracture hematoma even though it contains all the osteocompetent cells, and also molecules such as the mitogenic substances, growth factors such as TGFβ, ubiquitous growth-regulating proteins, and likewise PDGF. This hematoma also contains the osteoinductive factors BMP, FGF, IGF, and also the important elements in the form of the pericytes which, released from the basal lamina of the endothelium of the capillaries damaged by the fracture, become involved in the process of stimulation of angiogenesis, the synthesis of collagen, proteoglycans and osteocalcin, and in the initiation of phagocytosis.

The absence of all these factors will considerably slow down the production of the bone callus. Moreover, given the fact that, during the consolidation of an osteosynthesized fracture, the remodeling has to continue for at least 18 months, removal of the orthopedic material before this date, for whatever reason, increases the risks of complications such as fractures, pseudarthrosis or infection.

In conclusion, the removal of the osteosynthesis material, requiring a new surgery at a site that has already suffered trauma following a first aggressive surgery on the bone and on the surrounding tissues, generates cicatricial changes which disturb the recovery ad integrum of the initial anatomy and prevent the detection of the anatomical structures. All of this runs counter to the definition of osteosynthesis, which is a maneuver consisting of consolidating the fractured bone to the anatomical position without risking failure of the implant, all this notwithstanding the resulting socio-economic impact.

There is therefore a real need for osteosynthesis material that adjusts optimally to the fracture site, that can be kept there permanently and offers an alternative solution to the problems associated with the presence and/or the removal of the existing metallic osteosynthesis material, such as toxic release, metallosis of the periprosthetic tissues, systemic effects and weakening of the bone.

The inventors have shown that a material satisfying these needs can be obtained from a natural hybrid biomaterial which is the nacreous aragonitic layer of bivalve mollusks chosen from the group comprising *Pinctada maxima, Pinctada margaritifera, Tridacnae maxima, Tridacnae gigas* and other *Pinctada* species. They have also proven that this biomaterial can be used to produce osteosynthesis devices and implants such as: osteosynthesis plates and screws, osteotomy wedges, diabolos, intersomatic wedges and cages, intramedullary nails, humeral and femoral heads, glenoid cavities, tibial plateaus, femoral condyles, vertebral bodies, semi-maxillaries, bones of the ossicular chain, surgical anchors for ligament and/or tendon reinsertion, splints for osteosynthesized reduction of small-fragment comminuted fractures, membrane retention screws and dental implants acting as permanent autologous grafts.

The nacreous aragonitic layer of bivalve mollusks chosen from the group comprising *Pinctada maxima, Pinctada margaritifera, Tridacnae maxima, Tridacnae gigas* and other *Pinctada* species is an organic and inorganic composite material of biogenic origin and of hybrid structure. Indeed, the nacreous aragonitic layer of these bivalve mollusks is presented in the form of a layered architecture alternating between a mineral component consisting of nanocrystals of aragonite, calcium carbonate crystallized in the orthorhombic system, organized in sheets, and an organic component consisting of linear and branched biopolymers organized in a three-dimensional lattice. This assembly gives the biomaterial a lamellar architecture particularly adapted to the absorption and distribution of the forces and impacts opposing rupture.

It has been shown that the strength of a lamellar structure is associated with the organic component, and the rigidity with the mineral component, and that the polymers present the ideal structure for absorbing and dissipating the energy-to-break. However, the process of development and growth of the valves, especially of the nacreous aragonitic layer, may be modified due to endogenic factors, such as the physiology and physiopathology, which differ from one mollusk to another, and to exogenic factors such as the biotope, variations in the marine environment, the temperature of the water, the composition of the zooplankton and phytoplankton, the aggression of the pathogenic agents and predators.

This results in an alteration of the macro-, micro- and nanometric architectural arrangement of the components and, consequently, of the quality of the aragonite, with repercussions on the mechanical properties which, for this reason, are not reproducible from one valve to another.

It has been possible to show by engineering that an arrangement of structures in a ratio of 10/1, that is to say a ratio of 400 nanometers of hard structures for 40 nanometers of soft structures, constituted the standard for the production of hybrid lamellar structures, giving rise to the production of bioinspired synthetic materials of the aragonitic type, reproducing the alternating organization of organic-inorganic interfaces, to obtain a three-dimensional material such as the marine aragonite of the mollusks mentionned above.

Moreover, the particular nature of the organic lattice, separating and uniting the inorganic sheets of aragonite, lies in the fact that it has interconnected pores of different diameters communicating throughout its thickness, giving it a continuous porosity and an open porosity with open pores.

Bone is a viscoelastic material of which the viscous character is due to the presence of the interstitial fluids which impregnate it, and particularly to that of the biopolymers such as the collagens, glyosaminoglycans and proteoglycans included in its composition.

The viscoelastic properties are more considerable in a fresh cortical bone, that is to say one impregnated with interstitial fluids (plasma, serum, etc.), than in dry bone. The same is true of the nacreous aragonitic layer of mollusks, the subject matter of the invention, which, even when dry, contains 2 to 3% water, mainly located in the biopolymer layers of which it is composed.

French patent No. 09 54066 and U.S. Pat. No. 8,485,458 have described how the organic fraction of the nacreous aragonitic layer of the bivalve mollusks chosen from the groups comprising *Pinctada maxima, Pinctada margaritifera, Tridacnae maxima, Tridacnae gigas* and other *Pinctada* species, contains diffusible and soluble molecules having osteogenic properties which are involved in the growth and mineralization of calcified tissues. It also contains biopolymers composed largely of type I and II collagens, low molecular weight glycoproteins, of which some are related to growth factors, to cytokines and other osteocompetent molecules involved in the regeneration of bone and/or cartilage. This organic fraction also contains almost all the amino acids and in particular arginine, glycine, aspartic acid, molecules having chemotactic properties favoring cell adhesion, and also metalloenzymes, metalloporphyrins, metalloproteins, molecules involved in numerous metabolic reactions during osteogenesis. In addition to the calcium carbonate, the mineral fraction also contains numerous minerals, and also metals involved in the biosynthesis of the calcified tissues.

The inventors have shown (C.R. Acad. Sc. Paris 1988, C.R. Acad. Sc. Paris 1989, CLINICAL MATERIAL 0267-6605/90/S03-50 1990) that the biomaterial perpetuated itself at the endosseous site, forming a tight welding with the receiving bone. Moreover, the active molecules contained in the aragonite of the abovementioned mollusks have no cytotoxic effect, no mutagenic effect and no systemic effect, their interaction having only the impact of potentiating and stimulating local factors of cicatrization and bone regeneration.

It has been possible to demonstrate in biomechanics, i.e. the study of the mechanical properties of the bones, that there was a close relationship between their three-dimensional structure, their anatomical positioning and their functions. The spatial and temporal responses are thus adapted to the internal and external forces and stresses, the loads applied to the osseous structures being different depending on their functions and their anatomical positioning.

The mechanical properties of the bones are therefore different depending on their shapes, their functions and their relation to the different musculoskeletal levels. The values of the different types of measurement of strength, such as Young's modulus, flexural or compressive breaking strength, elongation at break, thus vary depending on whether they are applied to long bones, such as the femur, the tibia, the fibula, the humerus, the radius and the cubitus, to short bones, such as those of the carpus, metacarpus, tarsus and metatarsus, to skeletal masses, such as the vertebral bodies, the bones of the pelvis, and to the flat bones, such as those of the face and cranium, and also the clavicle and scapula.

It is also known that the behavior of the interface between the bone and the osteosynthesis plate or implant is non-linear and that the loads applied are dynamic. This is why the behavior of an osteosynthesis device will be different depending on the anatomical positioning of the bone concerned.

It has also been demonstrated that the aragonite of the valves of the cited mollusks has mechanical properties for which the measurement parameters (Young's modulus, flexural or compressive breaking strength) have values which vary considerably and are clearly depending on the geographical origin, the biotope, the variations in the marine environment, the temperature of the water, and the composition of the zooplankton and of the phytoplankton. It is possible to observe that there is a matching between the scale of diversity of the values of these parameters and that of the mechanical properties of the bone, depending on its function and its positioning, as is explained above.

For the production of osteosynthesis devices and/or implants made of aragonite from the valves of the cited mollusks, the inventors therefore propose selecting them, according to their origin and the culture conditions, from the populations presenting values of mechanical parameters compatible with and adapted to the purposes of the osteosynthesis devices and implants envisioned.

The inventors have shown that the osteoclastic activity, at the source of the osseous reorganization, took place in the same way in respect of the biomaterial, at the interface between the bone and the biomaterial, but was limited in time and coupled to the concomitant activity of apposition of bone newly formed by the osteoblasts. In other words, this biological phenomenon confirms the osteomimetic nature of the biomaterial and explains why, at the endosseous site, it joins to the receiving bone.

Physiologically, one observes a release and stimulation, in situ, of all the cellular signals and molecules necessary for inducing the biological cascade involved in the reorganization of the damaged host tissue.

Moreover, in the field of odontostomatology, where the losses of substance are common after extraction, and in periodontal diseases where the use of bone substitute is proposed, the technique consists in using resorbable or non-resorbable membranes, which requires the use of retention screws, in most cases made of titanium or of stainless steel, in order to hold them in place and to form a space necessary to protect the bone substitute below the membrane. It is known that maintaining a bone filler material at the site is difficult, especially if it is in the form of granules, since it is expelled through the incision line or the fibrous mucosa. In order to maintain the filler material and the membrane in place, mini-screws made of titanium are used so as to form a space above the zone that is to be filled. The protocol involves removing these screws after cicatrization and bone regeneration, with ablation of the membrane if non-resorbable.

Similarly, in oral implantology, where most of the implants are made of titanium oxide and zirconium, the same biological signs are observed as with the osteosynthesis materials and the fixation screws, which signs are indicated above.

SUMMARY

For these reasons, the inventors have developed a novel semi-synthetic hybrid material permitting the production of osteosynthesis devices and implants intended to be kept permanently in place at the fracture site, such as: osteosynthesis plates and screws, osteotomy wedges, diabolos, intersomatic wedges and cages, intramedullary nails, humeral and femoral heads, glenoid cavities, tibial plateaus, femoral condyles, vertebral bodies, semi-maxillaries, bones of the ossicular chain, surgical anchors for ligament and/or tendon reinsertion, splints for osteosynthesized reduction of small-fragment comminuted fractures, and also membrane retention screws and dental implants acting as permanent autologous grafts.

Thus, the invention relates to a semi-synthetic hybrid material, which is the nacreous aragonitic layer of bivalve mollusks chosen from the group comprising *Pinctada maxima, Pinctada margaritifera, Tridacnae maxima, Tridacnae gigas* and other *Pinctada* species, wherein said semi-synthetic hybrid material comprises an inorganic fraction and a cross-linked organic fraction having a pH from 7 to 7.4. The present invention also relates to the method for obtaining this material by structural modification of a natural hybrid biomaterial, which is the nacreous aragonitic layer of bivalve mollusks chosen from the group comprising *Pinctada maxima, Pinctada margaritifera, Tridacnae maxima, Tridacnae gigas* and other *Pinctada* species. The present invention also relates to the methods for producing osteosynthesis devices and implants.

BRIEF DESCRIPTION OF THE DRAWINGS

FIGS. 1a, 1b and 1c illustrate, respectively, a view of the outer face, a side view and a view of the inner face of a straight osteosynthesis plate.

FIGS. 2a, 2b and 2c illustrate, respectively, a view of the outer face, a side view and a view of the inner face of a epiphyseal-dialphyseal osteosynthesis plate.

FIGS. 9a and 9b illustrate, respectively, a front view and a side view of an intramedullary nail.

FIGS. 11a and 11b illustrate, respectively, a sagittal section and an exploded view of a dental replacement implant.

DETAILED DESCRIPTION

Figures 3A, 3B, 3C:
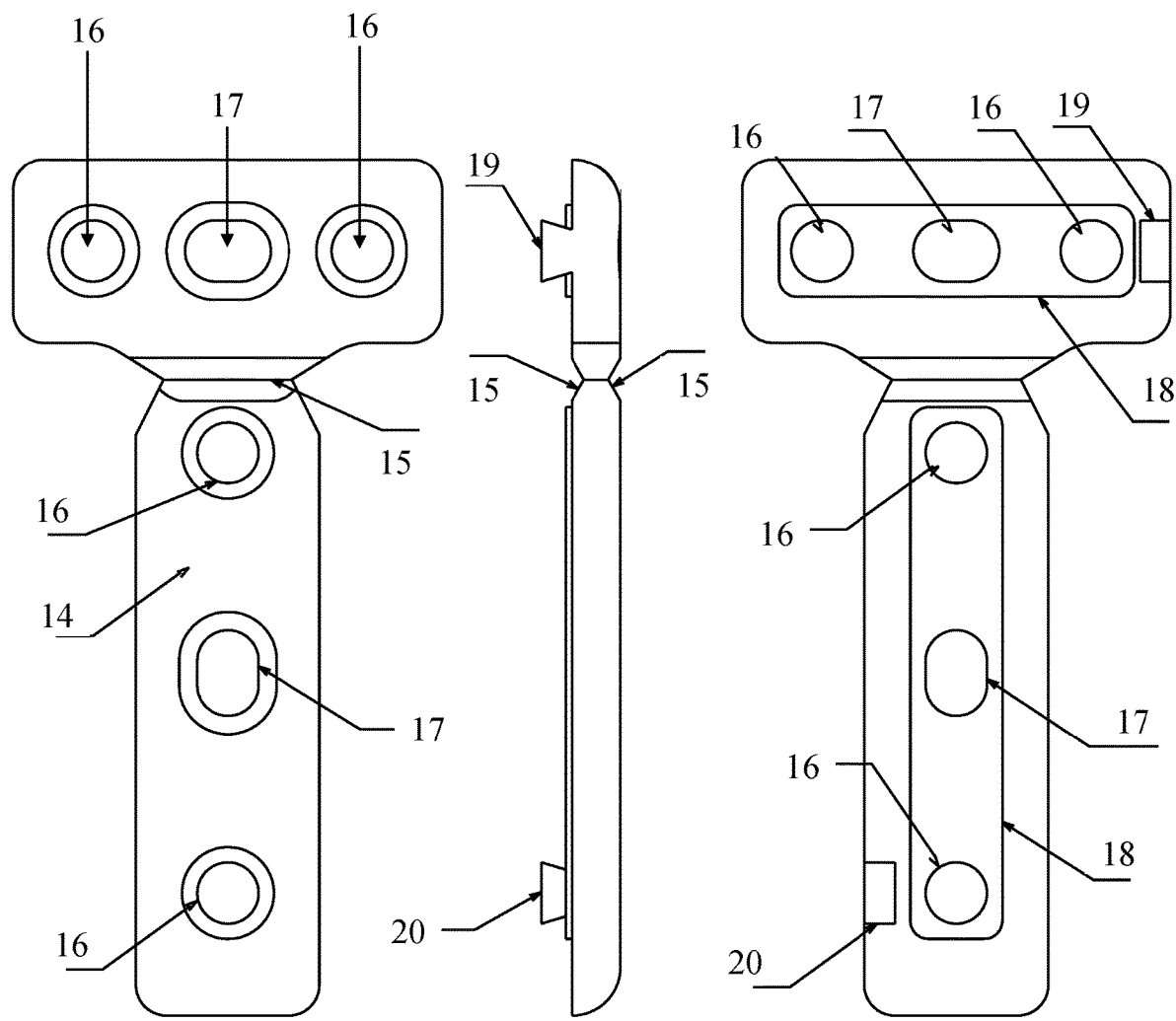
FIGS. 3a, 3b and 3c illustrate, respectively, a view of the outer face, a side view and a view of the inner face of a epiphyseal-dialphyseal osteosynthesis break plate.

According to a first aspect, the invention relates to a semi-synthetic hybrid material which is the nacreous aragonitic layer of bivalve mollusks chosen from the group comprising *Pinctada maxima, Pinctada margaritifera, Tridacnae maxima, Tridacnae gigas* and other *Pinctada* species, wherein said semi-synthetic hybrid material said material comprising an inorganic fraction and a cross-linked organic fraction and having a pH from 7 to 7.4.

Due to its chemical composition, and its variable structural properties that depend on the characteristics of its place of origin and culture, the semi-synthetic hybrid material of the invention has, particularly by comparison with those of titanium or steel, suitable mechanical properties compatible with the different types of cortical bone.

The semi-synthetic hybrid material has a layered structure, i.e., a superposition of inorganic fractions and organic fractions. In particular, the organic fraction does not include mineral inclusions.

The semi-synthetic hybrid material is not synthesized, but is obtained by modification of the textural and structural properties of the nacreous aragonitic layer of bivalve mollusks chosen from the group comprising *Pinctada maxima, Pinctada margaritifera, Tridacnae maxima, Tridacnae gigas* and other *Pinctada* species, in particular a pH modification and a cross-linkage of the organic layer.

The pH of the semi-synthetic hybrid material of the invention is measured on an aliquot of the material reduced to powder and dispersed in water. The pH of the semi-synthetic hybrid material of the invention is close to the pH of the biological fluids and of the inner environment (which is at about 7.4), and this will allow the osteosynthesis devices and/or implants produced from this material to be well tolerated and undergo a perfect biological integration. Moreover, such a pH creates conditions favoring the induction of cross-linking of the biopolymer chains of the organic fraction of the hybrid material.

The cross-linking is characterized by a multidirectional interconnection of the chains of the linear and branched biopolymers constituting said organic fraction. The cross-linking induces a high cohesion energy, an increase in the surface energy and, consequently, an increase in the adhesiveness and hydrophilicity of the semi-synthetic hybrid material of the invention. It also has the purpose of increasing the resistance of the organic fraction of the biomaterial to the corrosive action of the biological fluids, by reducing its solubility and by opposing its ageing, and to the action of the mechanical stresses to which the biomaterial is subjected.

These structural modifications also create conditions favoring the impregnation of the osteosynthesis device and/or implant, produced from the semi-synthetic hybrid material of the invention, by biological liquids and/or compositions containing pharmaceutically active substances.

The invention also relates to a method for producing a semi-synthetic hybrid material from a natural hybrid biomaterial, which comprises an inorganic fraction and an organic fraction, said method comprising a step of modifying the pH and a step of cross-linking the organic fraction of said hybrid biomaterial.

In the method of the invention, the natural hybrid biomaterial is the nacreous aragonitic layer of bivalve mollusks chosen from the group comprising *Pinctada maxima, Pinctada margaritifera, Tridacnae maxima, Tridacnae gigas* and other *Pinctada* species.

The mechanical tests carried out on samples of aragonite from the bivalve mollusks concerned, examining among other things Young's modulus or the breaking strenght, have shown that this biomaterial has, depending on its geographical origin and its culture conditions, a wide range of values compatible with the production of osteosynthesis material and implants depending on their purpose, that is to say the type of bone concerned.

To ensure that, depending on the origin and the culture conditions initially found, the observed mechanical properties of the biomaterial are preserved around the mean values compatible with its use as osteosynthesis material and/or implant material for a type of bone concerned, it was therefore necessary to find a method capable of structurally reinforcing the biomaterial so that its essential mechanical properties are preserved according to the purpose of the osteosynthesis device and/or implant to produced.

According to the layered hybrid nature of the aragonite of the previously cited mollusks, the inventors thus propose to subject its biopolymer component to a specific polymeric treatment to modify the structure of the aragonite, thus resulting in a reinforcement of its mechanical properties.

Indeed, in engineering and in particular in the chemistry of polymer plastics, it has been shown that the cross-linking consolidates the mechanical properties. This is why the inventors propose a method of cross-linking, particularly by riboflavin, of the collagenic fractions, of the proteoglycans and glycosaminoglycans of the organic fraction of the valves of the cited mollusks, by reference to the cross-linking of corneal collagen, which is a biochemical fibrillar bridging by covalent bonds.

In order to be able to use the natural hybrid biomaterial for producing osteosynthesis devices and/or implants, the inventors have found that it was important to consolidate its original mechanical properties by cross-linking the chains of the biopolymers composing its organic fraction. To do this, it was first of all necessary to lower its pH, generally of between 9 and 12, to a level of between 7 and 7.4, close to that of the circulating biological fluids, thereby favoring the tolerance and biological integration of the osteosynthesis devices and/or implants on and in the receiving site.

According to a particular embodiment, the step of modifying the pH is performed by immersion in a bath of microbiologically controlled mains water, brought to boiling point, for example in a mixture of equal parts of microbiologically controlled mains water and osmosed water, until the desired pH is obtained. The treatment lasts, for example, for 60 to 180 minutes, preferably 60 to 120 minutes. The pH can be measured on an aliquot of the biomaterial reduced to powder and dispersed in water.

According to a particular embodiment, the cross-linking step is performed with the aid of a cross-linking agent such as riboflavin, vitamin C, a polyol such as mannitol, and/or with the aid of physical agents such as ionizing radiation.

The invention also relates to a method for producing an osteosynthesis device or implant made of semi-synthetic hybrid material as defined above. Said method comprises the following steps:

a) selecting valves, having previously undergone exposure of their nacreous aragonitic layer, of the mollusks chosen from the group comprising *Pinctada maxima*, *Pinctada margaritifera*, *Tridacnae maxima*, *Tridacnae gigas* and other *Pinctada* species,
 b) cutting out pre-forms and producing the osteosynthesis material, if appropriate after digital modeling,
 c) modifying the pH and cross-linking, and
 d) modifying the surface state, the order of steps b) and c) being inconsequential.

Step a) involves selecting a mollusk valve according to its origin and its culture conditions, but also according to the purpose of the envisioned osteosynthesis material, said valve having a thickness and a physical and structural integrity that allow a pre-form of a size adapted to the envisioned device to be cut out from the previously exposed nacreous aragonitic layer.

In order to expose the nacreous aragonitic layer, the periostracum and the external prismatic calcitic layer are ground by abrasion, in particular with the aid of a fine-grain diamond wheel, for example at a speed of 3,000 rpm under a stream of water. The thickness is measured with the aid of calipers. The physical and structural integrity of the aragonitic layer of the selected valve is checked in an optical chamber, for example with the aid of a halogen light source of 500 watt.

The valve is then brushed and washed under a stream of microbiologically controlled mains water at a temperature of 55° C.

Step b) of cutting and production comprises, in a first phase, cutting out pre-forms intended to produce osteosynthesis devices according to previously imprinted contours, on one or the other of the faces of the valve, to the dimensions of said devices.

According to a suitable embodiment, this cutting phase of step b) is performed using a water jet charged with abrasive. The cutting with a water jet charged with abrasive has the advantage of not causing vibrations that may generate the start of microfractures, and of not causing exothermic reactions capable of degrading the hybrid material.

Advantageously, the abrasive will be composed of grains of aragonite, thereby preventing any contamination of the material by a material of another nature.

For example, the cutting can be carried out in the following way: said valve is placed in suitable retaining frames, which are fixed on the belt of a cutting machine, for example with 5 axes, using a water jet charged with abrasive. The abrasive can be composed of grains of aragonite with a grain size of between 0.1 and 200 μm. The water charged with abrasive grains is pulsed at a pressure of 4,000 to 6,200 bar, with the aid of focusing guns of 0.50 to 1.2 mm in diameter, and cutting nozzles of 0.12 to 0.40 mm in diameter.

The second phase of step b) involves production by precision-grinding or turning of the osteosynthesis devices and/or implants, optionally after digital modeling, permitting the exploitation of these data by digitally controlled machine tools.

According to a particular embodiment, the eventual insertion zone is digitally modeled on the basis of anatomical components, such that the geometry of the inner face of the osteosynthesis device or implant to be produced adapts as closely as possible to the topography of this zone. The osteosynthesis device or implant is thus produced in a homologous manner for a right or left limb.

According to another particular embodiment, drawings and sketches of the devices are digitized in order to permit production thereof by turning or precision-grinding.

The phase of production by precision-grinding or turning in step b) can be carried out, according to a particular embodiment, by means of digitally controlled machine tools using diamond-tipped or ceramic abrasive rotary instruments.

According to another particular embodiment, for the devices concerned, the phase of surface precision-grinding in step b) can be carried out with the aid of a micro-cutting with a jet of charged water machine tool.

Step c) of modifying the pH and of cross-linking involves modifying the physical and chemical properties of the hybrid material.

According to a particular embodiment, the modification of the pH in step c) is performed by immersion in a bath of microbiologically controlled mains water, brought to boiling point, for example in a mixture of equal parts of microbiologically controlled mains water and osmosed water, until the desired pH is obtained. The treatment can last, for example, for 60 to 180 minutes, preferably for 60 to 120 minutes.

According to a particular embodiment, the cross-linking in step c) is performed with the aid of a cross-linking agent such as riboflavin, vitamin C or a polyol such as mannitol. Classically, cross-linking is performed at a temperature above 20° C. In the case where riboflavin is used, the impregnation of the hybrid biomaterial with the riboflavin will advantageously be able to be followed by actinic exposure to UVA. The cross-linking can also be obtained by use of physical agents such as ionizing radiation.

The inventors have favored the action of riboflavin, or vitamin B2, as cross-linking agent by virtue of its pharmacological, biochemical and physical properties. Indeed Riboflavin very easily withstands sterilization and freezing and stimulates the cell metabolism. Considered as a cell growth factor, it is involved in the synthesis of proteins, carbohydrates and lipids and has powerful antioxidant properties, which oppose the action of the free radicals produced by the actinic action during cross-linking. It will thus be seen that the use of hydrosoluble riboflavin has the effect not only of modifying the structure of the semi-synthetic material but also of conferring on it novel pharmacological properties beneficial to bone regeneration and cicatrization.

Step d) involves modifying the surface state of said osteosynthesis device or implant by applying four successive treatments of sandblasting, cleaning by ultrasound, cryogenics, and application of nanoparticles. The objective is, on the one hand, to improve the tribology properties, especially the strong bonds of the covalent type at the origin of the aggregation of the nanoparticles and of their interaction with the receiving medium, and, on the other hand, to increase the surface/volume ratio between the device and the fractured cortical bone in order to ensure the stability thereof, and finally to promote the release of the soluble osteogenerating molecules that activate the local factors of osteogenesis contained in them.

According to a particular embodiment, the sandblasting treatment in step d) involves modifying the surface state of the osteosynthesis device or implant in order to improve the anchoring thereof to the bone.

For example, it can be carried out in the following way: said device is placed in a sandblaster and treated by being successively sprayed, with the aid of an overpressure system, preferably with grains of aragonite measuring from 25 to 70 μm propelled with the aid of round sandblasting nozzles measuring 0.8 mm, and with grains of aragonite measuring from 70 to 250 μm propelled with the aid of nozzles measuring 1.2 mm, at a pressure of 6 bar.

According to a particular mode of treatment, the cleaning by ultrasound in step d) is carried out as follows: an ultrasonic bath is filled with microbiologically controlled hot mains water, at 55° C., which is the temperature of maximum efficiency, up to a marker indicating the desired volume of water. To this is added a cleaning and disinfecting solution at a dilution of 1:128, i.e. 1 part of solution for 127 parts of water. After 15 minutes of degassing, intended to remove the air bubbles, the osteosynthesis device or implant is placed in the bath for a duration of 30 minutes at a frequency of 40 kHz for a cavitation leading to optimal particle removal.

Said device is then rinsed under a stream of microbiologically controlled mains water for 20 minutes, then immersed for 20 minutes in a bath of demineralized water at a temperature of 90° C., to which is added 2% bleach at 2.6% active chloride for 30 minutes, then rinsed again with demineralized water at 90° C.

Finally, the device is left to soak in demineralized water at 50° C., to which is added liquid Calbénium®, or any other biocidal, virucidal or surface-active agent diluted to 2%, for 30 minutes, rinsed, then dried.

According to a particular embodiment, the non-abrasive cryogenic treatment in step d), which is intended to prepare the faces of the device in contact with the cortical bone, involves spraying onto these faces small balls of dry ice of liquid nitrogen at −80° C. and measuring 1 mm in diameter. The objective is to optimize the surface state by a mechanical effect associated with a thermal shock, on account of the difference in temperature between the surface to be treated and the balls of liquid nitrogen during the sublimation thereof upon impact. Inside a dedicated space, a mixture of compressed air and balls of ice are thus sprayed onto the one or more surfaces to be treated, at a pressure permitting a non-abrasive treatment optimized by the low hardness of the dry nitrogen ice, which is 2 Mohs.

According to the invention, the application phase of nanoparticles in step d) for modifying the surface state is a coating of mechanically structured nanoparticles that are obtained from the hybrid biomaterial, according to French patent No. 09 54066 and U.S. Pat. No. 8,485,458.

This phase of step d) for modifying the surface state is carried out either by immersion in an emulsion of variable viscosity of said mechanically structured nanoparticles, or by centrifugation, or by spraying, or, preferably, by electro-deposition, which involves plunging the osteosynthesis devices and the implants into an electrolytic bath of said nanoparticles, in such a way as to initiate an electro-deposition of said nanoparticles on the surface of the latter.

At the end of the physical and chemical treatments applied according to the method of the invention, the aragonite of the mollusks concerned, constituting the devices produced according to the invention, can be considered to have been transformed into semi-synthetic hybrid material.

According to a particular embodiment, the method for producing an osteosynthesis device and/or implant additionally comprises a step e) involving impregnation thereof by biological liquids and/or compositions containing pharmaceutically active substances.

In order to standardize the viscoelastic properties of the osteosynthesis devices and implants produced according to the invention, the inventors therefore propose that the biopolymers included in their composition are impregnated with plasmas or serums of the different antigenic systems of the blood groups, by soaking and/or impregnation, at atmospheric pressure or under vacuum, which additionally increases their biological acceptance.

In another preferred embodiment, the devices and implants can be impregnated by medicinal substances such as non-steroidal anti-inflammatories, analgesics, antibiotics and antimitotics, or any other substance having a therapeutic effect.

According to a particular embodiment, the method for producing a device additionally comprises phases of packaging, for example in a double packaging, of sterilization, under a protective atmosphere, carried out with the aid of ionizing radiation at 25 KGy, and also a storage step, either at a temperature of 0° to 4° C. or by freezing at −15° C., or, for the devices that have not been impregnated by the biological liquids, storage at ambient temperature.

The devices can also be impregnated extemporaneously with whole blood or autologous plasma at the time of the surgery.

The invention also relates to a device made of semi-synthetic hybrid material, or obtained according to the method for producing said device. Said device is chosen from among osteosynthesis plates, such as a straight osteosynthesis plate, an epiphyseal-diaphyseal osteosynthesis plate, an osteosynthesis plate for malleolar fractures, an epiphyseal-diaphyseal osteosynthesis break plate, osteosynthesis screws, membrane retention screws, osteotomy wedges, diabolos, intersomatic wedges and cages, intramedullary nails, humeral and femoral heads, glenoid cavities, tibial plateaus, femoral condyles, vertebral bodies, semi-maxillaries, bones of the ossicular chain, surgical anchors for ligament and tendon reinsertion, splints for osteosynthe-sized reduction of small-fragment comminuted fractures, and dental implants.

According to a particular embodiment, the device has at least one retention means which, during the positioning of said device, opposes the displacement thereof, said means being chosen from among locking pins, notches, a keyed and flattened harpoon, and a thread against unscrewing.

According to the particular embodiment in which the retention means is formed by locking pins, these, being diametrically opposite, make it possible to lock said device on the bone fragments on each side of the fracture line, after insertion wells have been formed in the cortical bone for the locking pins with the aid of a dummy plate, thereby providing an immediate keyed primary fixation and a secondary fixation once the bone cicatrization has taken place.

According to the particular embodiment in which the retention means is formed by transverse rectilinear notches in a step shape, these notches, by virtue of their geometry, oppose forward or rearward sliding of said device.

According to the particular embodiment in which the retention means is a flattened keyed harpoon, the features of the latter oppose sliding and rotation of said device.

According to the particular embodiment in which the retention means is a thread, the latter has a geometry of non-metric pitch, and of trapezoidal shape, which opposes its unscrewing.

Advantageously, this thread favors total filling of the windings by the newly formed bone tissue.

According to a suitable embodiment, the device additionally comprises fixation holes. The number, size and location of these fixation holes will of course be adapted by the skilled person in accordance with the shape and dimensions of the device.

Said fixation holes can be milled, partially or entirely, and, if appropriate, tapped with an ISO metric thread of standard pitch or fine pitch.

According to a suitable embodiment, said fixation holes can be round or oblong and/or can form an acute angle with the vertical.

According to a particular embodiment, the device additionally comprises a means which, during the positioning of said device, permits the adjustment thereof in such a way as to adapt optimally to the morphology of the fracture site. According to a suitable embodiment, the means which, during the positioning of the device, permits the adjustment thereof is a bulge positioned on the inner face of said device with a height of between 0.1 and 0.5 mm, preferably of between 0.15 and 0.25 mm. It will be possible for this bulge to be ground as required just before the positioning.

According to a particular embodiment, the device, which is an epiphyseal-diaphyseal break plate, additionally comprises two V-shaped break notches, one on the outer face, the other on the inner face. The break notch on the outer face of the device is easily detectable to the touch and indicates the seat of the skin incision to be made. Said device can then be broken with the aid of a hammer and a surgical chisel, allowing the limb to continue its development, the two parts of said device moving away from each other as the conjugation cartilage evolves.

During the surgerys, all the osteosynthesis material produced according to the invention is positioned with the aid of ancillaries, comprising phantom plates made to the dimensions and to the characteristics of the osteosynthesis devices and having, among others, the following accessories: one or more drill bushes, depth gauges and holding gauges, drill bits and screw taps made to the dimensions of the screws, screw holders and plate holders, forceps for holding the fragments, screwdrivers and keys for hexagonal screw heads, distractors, opening wedges, holding wedges, etc.

The following examples illustrate the invention without implying any limitation, and a person skilled in the art will be able to implement all the methods of the invention each time he wishes to produce an osteosynthesis device or an implant.

EXAMPLES

Example 1: Method for Producing Osteosynthesis Devices

The valves from mollusks, in this example *Pinctada maxima*, which are chosen have a thickness, measured with the aid of calipers, sufficient for producing the desired osteosynthesis devices.

The periostracum and the external prismatic calcitic layer are ground by abrasion, with the aid of a fine-grain diamond wheel, at a speed of 3,000 rpm under a stream of water, which render possible the exposure of the nacreous aragonitic layer.

The physical and structural integrity of the chosen valves is checked in an optical chamber with the aid of a halogen light source of 500 watt.

The valves are then brushed and washed under a stream of microbiologically controlled mains water at a temperature of 55° C.

In order to obtain pre-forms with the dimensions calculated according to those of the osteosynthesis devices that are to be produced, the contours are imprinted on one or other of the faces of the selected valves. The valves are then cut along the drawn contours. To do this, the valves are placed in suitable retaining frames, which are fixed on the belt of a cutting machine with 5 axes, using a water jet charged with abrasive, for example grains of aragonite with a grain size of about 150 µm, pulsed at a pressure of 4,135 to 6,150 bar, with the aid of focusing guns of 0.50 to 1.2 mm in diameter, and cutting nozzles of 0.20 to 0.40 mm in diameter.

Rough pre-forms are thus obtained.

To ensure that the geometry of the inner face of the osteosynthesis device adapts as closely as possible to the topography of its possible zone of insertion, the latter is digitally modeled on an anatomical piece, by which means the osteosynthesis devices can be offered in an equivalent manner for a right or left limb.

The shapes and dimensions of the osteosynthesis devices are also digitally modeled from sketches. These digital data are then used in order to allow the osteosynthesis devices to be manufactured by precision-grinding or turning with the aid of digitally controlled machines. The precision-grinding of the osteosynthesis pieces, except for screws, can be carried out by application of a grinding process under a current of water, using diamond-tipped or ceramic abrasive rotary instruments.

The osteosynthesis screws for their part can be obtained by a process of turning under a current of water, with the aid of diamond-tipped or ceramic abrasive rotary instruments. The osteosynthesis devices are then immersed in a bath comprising a mixture of equal parts of microbiologically controlled mains water and osmosed water, brought to boiling point at 100° C., for a variable length of time depending on their thickness, for example 60 minutes, in order to bring the pH of the constituent hybrid biomaterial to a value of between 7 and 7.4.

The osteosynthesis devices are then immersed in a 5% solution of riboflavin for 48 hours, at a temperature in excess of 20° C., in order to cross-link the biopolymer chains of the organic fraction of the constituent hybrid biomaterial. The devices are then rinsed and thereafter placed for 20 minutes in a glass enclosure provided with UVA lamps with a wavelength of 365 nm, at an intensity of 2,300 µJ/cm$^2$. The osteosynthesis devices are then dried with a current of hot air at 40° C.

Examination under a scanning electron microscope shows a densification of the network of the biopolymer lattice of the constituent material.

In order to promote the anchoring of the osteosynthesis devices produced, the surface state of the parts intended to be in contact with the bone is modified. As a first step, the faces and edges are sandblasted in a sandblaster, using an overpressure system, successively with round sandblasting nozzles of 0.8 mm, with grains of aragonite measuring from 25 to 70 µm, then with nozzles of 1.2 mm, with grains of aragonite measuring from 70 to 250 µm, at a pressure of 6 bar.

The osteosynthesis devices are then treated by ultrasound as follows. An ultrasonic bath is filled with microbiologically controlled hot mains water, at 55° C., which is the temperature of maximum efficiency, up to a marker indicating the desired volume of water. A cleaning and disinfecting solution is then added at a dilution of 1:128, i.e. 1 part of solution for 127 parts of water. After 15 minutes of degassing, intended to remove the air bubbles, the osteosynthesis devices are placed in the bath for a duration of 30 minutes at a frequency of 40 kHz for a cavitation leading to an optimal particle removal.

The osteosynthesis devices are then rinsed under a stream of microbiologically controlled mains water for 20 minutes, then immersed for 20 minutes in a bath of demineralized water at a temperature of 90° C., to which is added 2% bleach at 2.6% active chloride for 30 minutes, then rinsed again with demineralized water at 90° C.

Finally, the osteosynthesis devices are left to soak in demineralized water at 50° C., to which is added a biocidal agent, for example liquid Calbénium®, or any other virucidal or surface-active agent diluted to 2%, for 30 minutes, rinsed, then dried.

Two successive treatments are then carried out on the osteosynthesis devices. The faces of the devices intended to be in contact with the cortical bone undergo non-abrasive cryogenic treatment. This treatment consists in the spraying of small balls of dry ice of liquid nitrogen at −80° C. and measuring 1 mm in diameter onto these faces, in order to optimize the surface state by a mechanical effect associated with a thermal shock, on account of the difference in temperature between the surface to be treated and the balls of liquid nitrogen during the sublimation thereof upon impact. In this technique, a mixture of compressed air and balls of ice are sprayed onto the one or more surfaces to be treated, at a pressure permitting a non-abrasive treatment optimized by the low hardness of the dry liquid nitrogen ice, which is 2 Mohs.

The devices are then subjected to a treatment in which they are coated with mechanically structured nanoparticles, which are obtained from the hybrid biomaterial, according to the patents FR No. 09 54066 and U.S. Pat. No. 8,485,458, for example by electro-deposition, which involves plunging the osteosynthesis devices into an electrolytic bath of said nanoparticles, in such a way as to initiate an electro-deposition of said nanoparticles on the surface of the osteosynthesis devices.

The osteosynthesis devices are then dried under a current of hot air at 40° C. for 30 minutes, packed in double packaging, sterilized under a protective atmosphere with the aid of ionizing radiation at 25 KGy, and stored at ambient temperature.

Example 2: Straight Osteosynthesis Plate

A straight osteosynthesis plate is obtained by the method described in Example 1. FIGS. 1a, 1b and 1c show, respectively, a view of the outer face, a side view and a view of the inner face of the straight osteosynthesis plate 1.

The straight osteosynthesis plate 1 is in the form of a parallelepiped of variable length, width and thickness. Its plane outer face, radiused all round its perimeter, is pierced with several open fixation holes 2, 3 of variable diameters, of which the most central one 3 is oblong in order to permit translation of the plate depending on the topography of the fracture site. The open fixation holes 2, 3 are tapped on the lower half of their height with an ISO metric thread of standard pitch or fine pitch, corresponding to the thread under the head of the fixation screws, and they are milled on their upper half. The outer edges of the plate are radiused all round the perimeter.

The inner face in contact with the bone has, along its entire length, a rounded bulge 4 having a maximum thickness of 0.2 mm and encompassing the screw fixation holes 2, 3.

This bulge is intended to allow the plate to be adjusted as closely as possible to the anatomical variations of the insertion site. Indeed, osteology shows that the bone anatomy is reproducible from one individual to another; the differences concern the anatomical reliefs and features represented by the tuberosities, the tubercles, the apophyses, the grooves, the lines and the fossae, of which the shapes and volumes may vary by a few tenths of millimeters. Moreover, given the nature of the semi-synthetic material according to the invention, it is possible during surgery to rework the surface of the bulge with the aid of a diamond-tipped rotary instrument under a stream of refrigerated sterile water, so as to adjust the plate as closely as possible to the topography of the insertion site, such that the interface between bone and plate is as intimate as possible.

On its inner face, the straight osteosynthesis plate 1 also has, along its greatest dimensions, two locking pins 5 of trapezoidal shape and of variable dimensions, one in the upper third, the other in the lower third, and which are diametrically opposite. The function of these locking pins is to lock the plate on the bone fragments on either side of the fracture line after insertion wells for the locking pins have been formed in the cortical bone with the aid of the dummy plate, thereby producing an immediate keyed primary fixation and a secondary fixation once the bone cicatrization has taken place.

Example 3: Epiphyseal-Diaphyseal Osteosynthesis Plate

An epiphyseal-diaphyseal osteosynthesis plate is obtained by the method described in Example 1. FIGS. 2a, 2b and 2c show, respectively, a view of the outer face, a side view and a view of the inner face of the epiphyseal-dialphyseal osteosynthesis plate 6.

The T-shaped epiphyseal-diaphyseal osteosynthesis plate 6 has a horizontal epiphyseal part of variable length, height and thickness, curved forward and inward in such a way as to match the meta-epiphyseal topography.

It is pierced with open fixation holes 7, 8 of variable number (three in FIG. 2a) and diameter, which are milled on their upper half and tapped on their lower half with a standard or fine ISO metric pitch.

The central fixation hole 8 of variable dimensions is oblong, in order to permit translation according to the requirements.

The vertical diaphyseal bar, which is of variable dimensions and has a slight convexity downward, inward and forward, matching the topography of the diaphyseal relief, is pierced with open fixation holes 9, 10 of variable number (three in FIG. 2a) and diameter, of which the central hole 10 is oblong in order to permit translation, if necessary, before tightening of the screws. These holes are milled in their upper half and tapped on the lower half with a standard or fine ISO metric pitch.

The outer edges of the plate are radiused all round the perimeter.

The outer faces of the epiphyseal and diaphyseal bars are plane.

The inner faces comprise a rounded bulge 11 having a maximum height of 0.2 mm and encompassing the fixation holes 7, 8, 9 and 10. They also have two locking pins 12, 13 which act as keys in the cortical bone and which are diametrically opposite, of trapezoidal shape and of variable dimensions, one 12 on the rear vertical edge of the epiphyseal bar, the other 13 in the lower third of the front edge of the diaphyseal bar, thereby opposing the rotation and shifting of the distal and proximal fragments of the fractured bone.

Example 4: Epiphyseal-Diaphyseal Osteosynthesis Break Plate

An epiphyseal-diaphyseal osteosynthesis break plate is obtained by the method described in Example 1. FIGS. 3a, 3b and 3c show, respectively, a view of the outer face, a side view and a view of the inner face of the epiphyseal-dialphyseal osteosynthesis break plate 14. This break plate is intended for use in pediatric surgery.

The epiphyseal-diaphyseal osteosynthesis break plate 14 is in the shape of a T of variable dimensions and is similar in all its features to the plate for adults in Example 3, and it also has on its two faces, at the junction between the horizontal bar and the vertical bar, two V-shaped notches 15 affecting the edges.

The horizontal and vertical bars are pierced with open fixation holes 16, 17 of variable number and diameter, which are milled on their upper half and tapped on their lower half with a standard or fine ISO metric pitch.

The central fixation hole 17 of the horizontal and vertical bars of variable dimensions is oblong, in order to permit translation according to the requirements.

The outer edges of the plate are radiused all round the perimeter.

The outer faces of the horizontal and vertical bars are plane.

The inner faces (shown in FIG. 3c) of the horizontal bar and of the vertical bar each comprise a rounded bulge 18 having a maximum height of 0.2 mm and encompassing the fixation holes 16, 17. They also have two locking pins 19, 20 which act as keys in the cortical bone and which are diametrically opposite, of trapezoidal shape and of variable dimensions, one 19 on the rear vertical edge of the horizontal bar, the other 20 in the lower third of the front edge of the vertical bar, thereby opposing the rotation and shifting of the distal and proximal fragments of the fractured bone.

The V-shaped notches 15 situated at the junction of the horizontal bar and of the vertical bar allow the plate to be broken into two parts. These notches will be easily detected by touch and will indicate the site where the skin incision is to be made.

The plate will then be able to be broken with the aid of a hammer and a surgical chisel, allowing the limb to continue its development, the two parts of the osteosynthesis material moving away from each other as the conjugation cartilage evolves.

Example 5: Osteosynthesis Plate for Malleolar Fractures

Figure 4A:
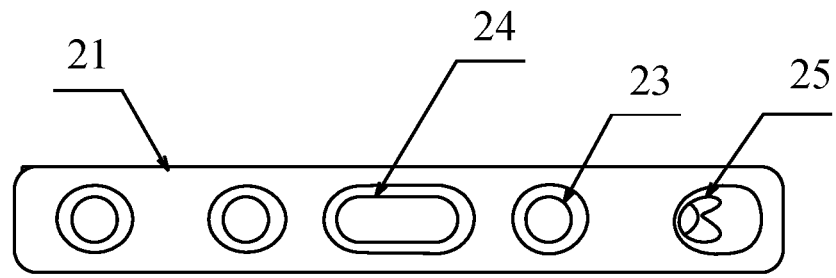
FIGS. 4a, 4b and 4c illustrate, respectively, a view of the outer face, an isometric view of the inner face and a side view of a osteosynthesis plate for malleolar fractures.
Figure 4B:
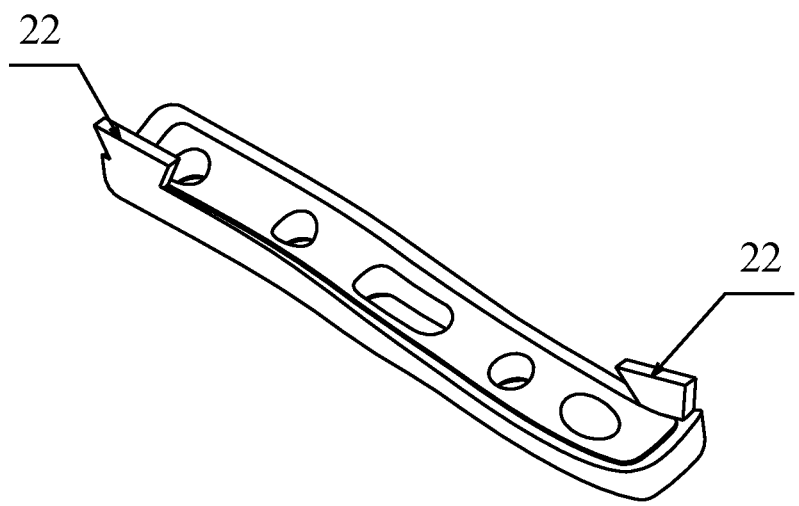
Figure 4C:

An osteosynthesis plate for malleolar fractures is obtained by the method described in Example 1. FIGS. 4a, 4b and 4c show, respectively, a view of the outer face, an isometric view of the inner face and a side view of the osteosynthesis plate 21 for malleolar fractures. The osteosynthesis plate 21 for malleolar fractures has the general shape of a parallelepiped of variable length and width, of which the lower end is convex rearward and upward along half of its length and radiused all round its perimeter.

Its inner face is forwardly concave and, at each end, has locking pins 22 of trapezoidal shape and of variable dimensions. The locking pin situated at the lower end is positioned in such a way as to fasten itself on the lower end of the styloid process once the fracture has been reduced.

The plate is pierced with fixation holes 23, 24, 25, which are variable in number depending on its length, and radiused all round its perimeter.

The most central hole 24 is of oblong shape in order to permit possible translation. The lower and last fixing hole 25 forms an angle of 15° with the vertical in order to permit fixation of the styloid process on the distal part of the fibula with bicortical support.

Example 6: Splint for Osteosynthesis of Comminuted Diaphyseal Fractures

Figure 5A:
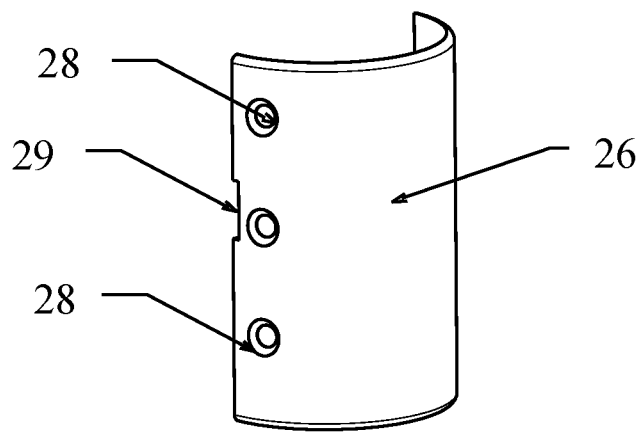
FIG. 5a illustrates the outer face of a half-sleeve of a splint for osteosynthesis of comminuted diaphyseal fractures.
Figure 5B:
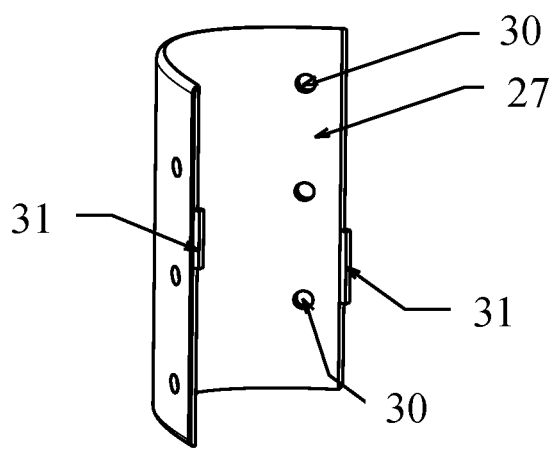
FIG. 5b illustrates the inner face of a half-sleeve of a splint for osteosynthesis of comminuted diaphyseal fractures.
Figure 5C:
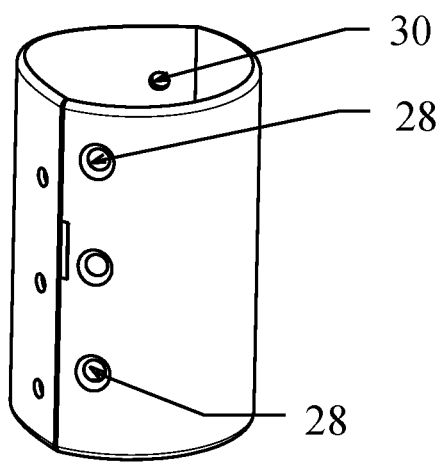
FIG. 5c illustrates the overall splint for osteosynthesis of comminuted diaphyseal fractures assembled.

A splint for osteosynthesis of comminuted diaphyseal fractures is obtained by the method described in Example 1. It is shown in FIGS. 5a, 5b and 5c. It is composed of two parts, being two half-sleeves 26, 27 which are machined on the basis of modeling of the possible zones of insertion of the osteosynthesis device. The outer face of the half-sleeve 26 is shown in FIG. 5a, and the inner face of the half-sleeve 27 is shown in FIG. 5b. The overall splint assembled from the two half-sleeves is shown in FIG. 5c.

The half-sleeve 26 is in the shape of a semicylinder of variable diameter and length, its outer face is convex over its entire height, pierced with open fixation holes 28 which are of variable number and diameter and which are aligned on the longitudinal edges of the splint and are offset with respect to each other in such a way that the fixation screws intersect. The fixation holes 28 are tapped on the inner half of their height with an ISO metric pitch and are milled on the other half. The inner face is concave over its entire height; it has, along the longitudinal edges, two diametrically opposite notches 29, one in the upper third, the other in the lower third.

The other half-sleeve 27 is machined on the basis of digital modeling of the equivalent zone of the half-sleeve 26 and is of generally triangular section, adapting to the bone morphology of the diaphyseal zone in question. It has a length and a thickness comparable to those of the half-sleeve 26 and is pierced with open fixation holes 30 which are tapped over their entire height with the ISO metric pitch corresponding to the thread of the end of the fixation screws. These holes are paired up with the holes 28 of the half-sleeve 26 and are diametrically opposite. Along its longitudinal and diametrically opposite edges, it has two locking pins 31 of variable dimensions, corresponding to the notches 29 of the half-sleeve 26.

FIG. 5c shows the two half-sleeves joined together, the locking pins 31 of the half-sleeve 27 being fixed in the notches 29 of the half-sleeve 26.

The two half-sleeves 26, 27 are beveled in such a way as to conform to each other during osteosynthesis, and their upper and lower edges are radiused.

Example 7: Osteosynthesis Screw

Figure 6A:
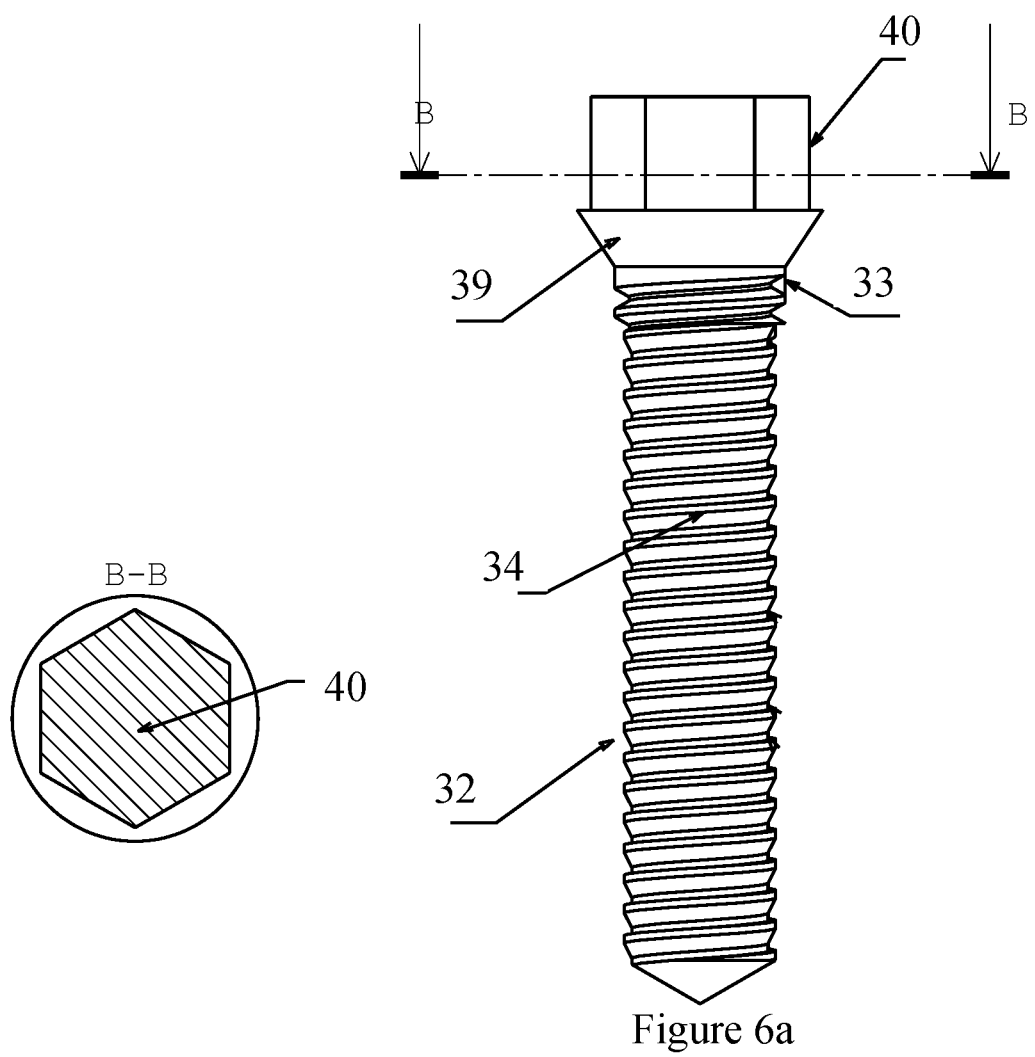
FIGS. 6a and 6b illustrate, respectively a view of a osteosynthesis screw and a pitch.

An osteosynthesis screw is obtained by the method equivalent to that described in Example 1. FIG. 6a shows a view of the osteosynthesis screw 32.

The osteosynthesis screw 32 has an overall cylindrical shape composed of a thread and of a head, which are of different diameters and of variable dimensions.

The upper end 39 of the screw is milled and surmounted by a hexagonal device 40 allowing it to be screwed using a suitable ancillary tool.

The part 33 below the head is threaded with a standard or fine ISO metric pitch corresponding to the pitch of the inner part of the fixation holes of the plates.

The part 34 of the screw below the ISO metric thread is threaded with a particular pitch and has a geometry suitable, on the one hand, for opposing unscrewing and, on the other hand, for promoting the complete filling of the windings by the newly formed bone tissue.

Figure 6B:
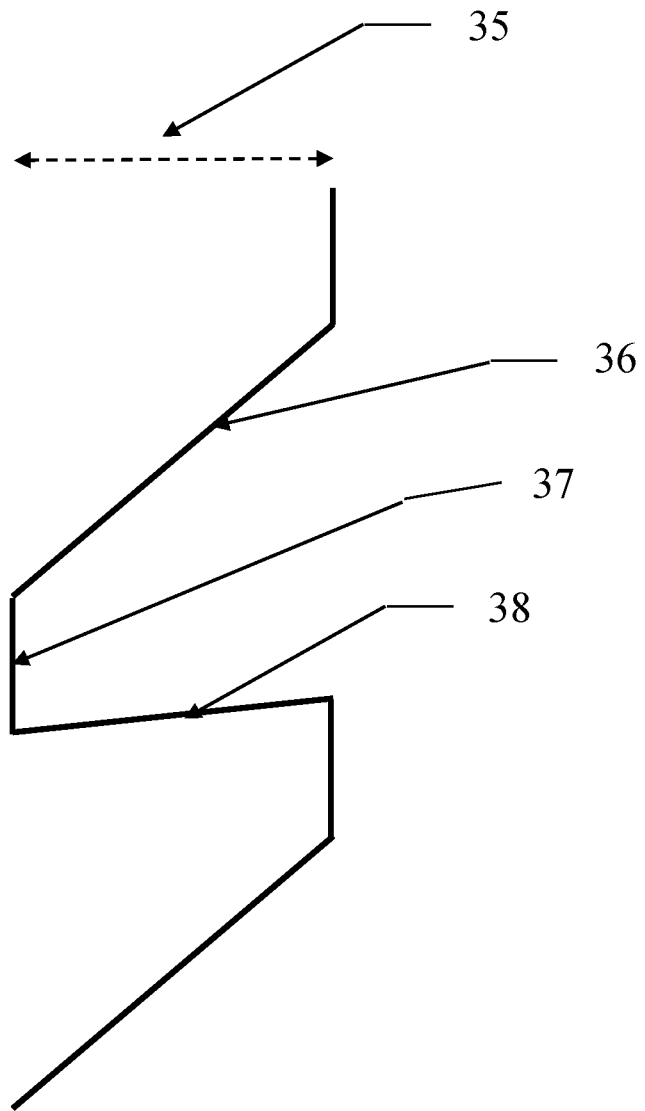

This pitch is shown in FIG. 6b. With a depth 35 of 0.40 mm, it has the shape of a trapezoid of which the inward and downward oblique upper side 36 forms an angle of about 135° with the upper end of the thread bottom 37, and of which the inward and downward oblique side 38 forms an angle of about 80° with the lower end of the thread bottom 37.

Example 8: Surgical Anchor for Ligament and/or Tendon Reinsertion

Figure 7:
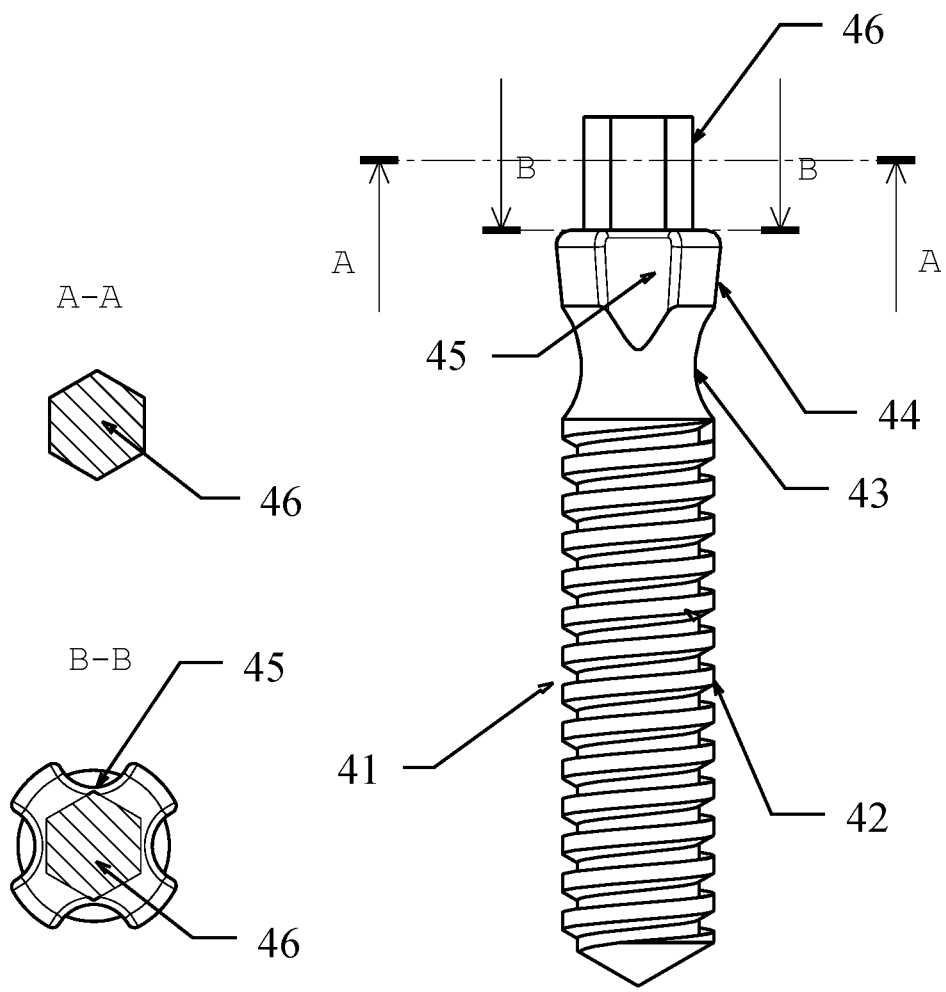
FIG. 7 illustrates an overall view of a surgical anchor for ligament and/or tendon reinsertion.

A surgical anchor for ligament and/or tendon reinsertion is obtained by the method described in Example 1. FIG. 7 shows an overall view of the surgical anchor 41 for ligament and/or tendon reinsertion.

The surgical anchor 41 for ligament and/or tendon reinsertion has an overall cylindrical shape and has, on the lower two thirds, a thread 42, such as described in FIG. 6b, opposing unscrewing.

The upper third, starting from the upper limit of the thread 42, has a circular constriction 43 of variable depth and height, surmounted by a quadrilateral 44 with radiused corners, having on its four faces a rounded depression 45 of variable diameter.

The quadrilateral 44 is surmounted by a hexagonal structure 46 of variable height, inscribed within the perimeter thereof.

Example 9: Intersomatic Cage

Figure 8A:
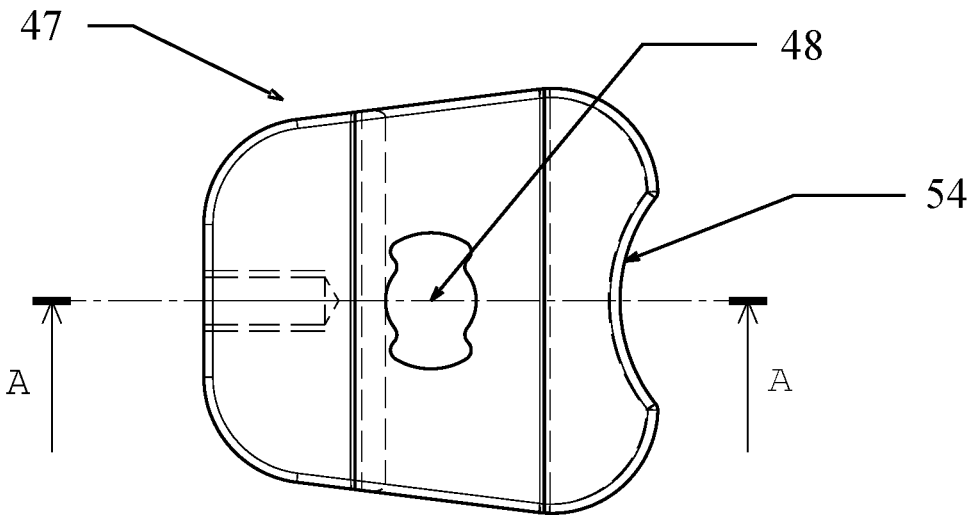
FIGS. 8a, 8b and 8c illustrate, respectively, the lower face, a sagittal section and the upper face of an intersomatic cage.
Figure 8B:
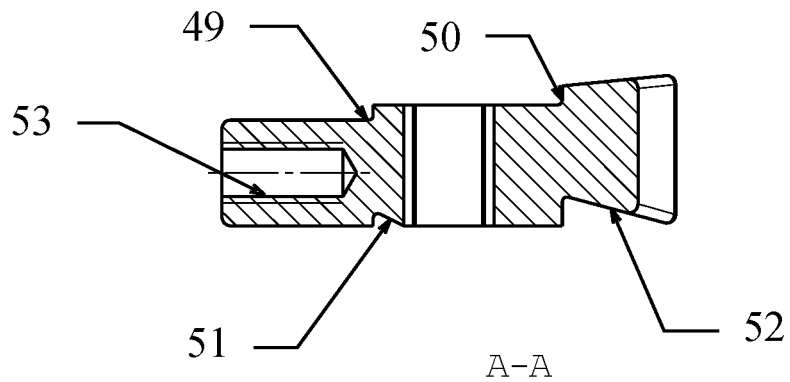
Figure 8C:
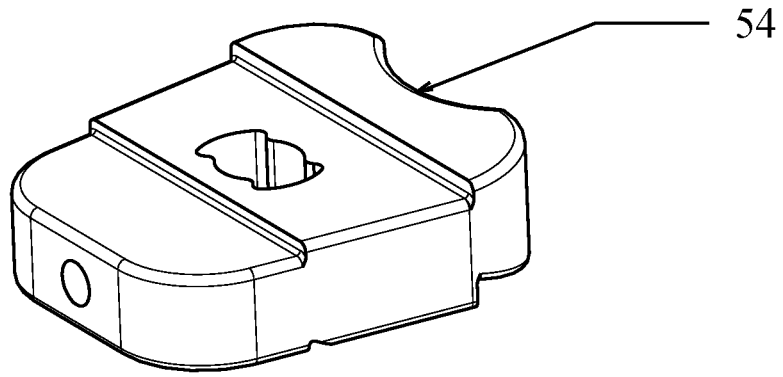

An intersomatic cage is obtained by the method described in Example 1. FIGS. 8a, 8b and 8c show, respectively, the lower face, a sagittal section and the upper face of the intersomatic cage 47.

The intersomatic cage 47 has the general shape of a parallelepiped with a trapezoidal base and of variable dimensions, of which the central part is pierced by an open orifice 48 of variable diameter, dovetailed in the transverse direction.

The plane upper face has two transverse rectilinear notches 49, 50 with a step shape, one 49 at a distance from and in front of the front edge of the central orifice, the other 50 at a distance from and behind the rear edge of the latter. These notches oppose forward sliding of the cage.

The plane lower face also has two notches 51, 52 inclined downward and rearward, one 51 at a distance from the front edge of the central orifice, the other 52 at a distance from the rear edge of the latter, opposing rearward sliding of the cage.

The upper face is machined at a predetermined angle depending on the site of the diskectomy and in such a way as to re-establish cervical or lumbar lordosis.

The plane front face, of variable dimensions, is pierced at its center by a fixation hole 53 which is tapped with an ISO metric pitch and is of variable depth and diameter, intended to receive firstly the cage-holding screw driver and secondly the fixation screw for the osteosynthesis plate.

The rear face, of variable height, has a rounded central depression 54 intended to be positioned opposite the yellow ligament.

All the edges and corners of the upper and lower faces of the intersomatic cage 47 are radiused.

Example 10: Intramedullary Nail

An intramedullary nail is obtained by the method described in Example 1. FIGS. 9a and 9b show, respectively, a front view and a side view of the intramedullary nail 55.

The intramedullary nail 55 is in the shape of a cylinder of variable diameter and length and, at both ends, has two or more through-orifices 56 allowing it to be keyed in place with the aid of bicortical support screws.

The lower end 57 is harpoon-shaped and has two diametrically opposite flats 58.

The upper end 59 is rounded and flattened at the center so as to allow impaction, and it has, all round its diameter, a shoulder 60 with radiused perimeter.

Example 11: Membrane Retention Screw

Figure 10:
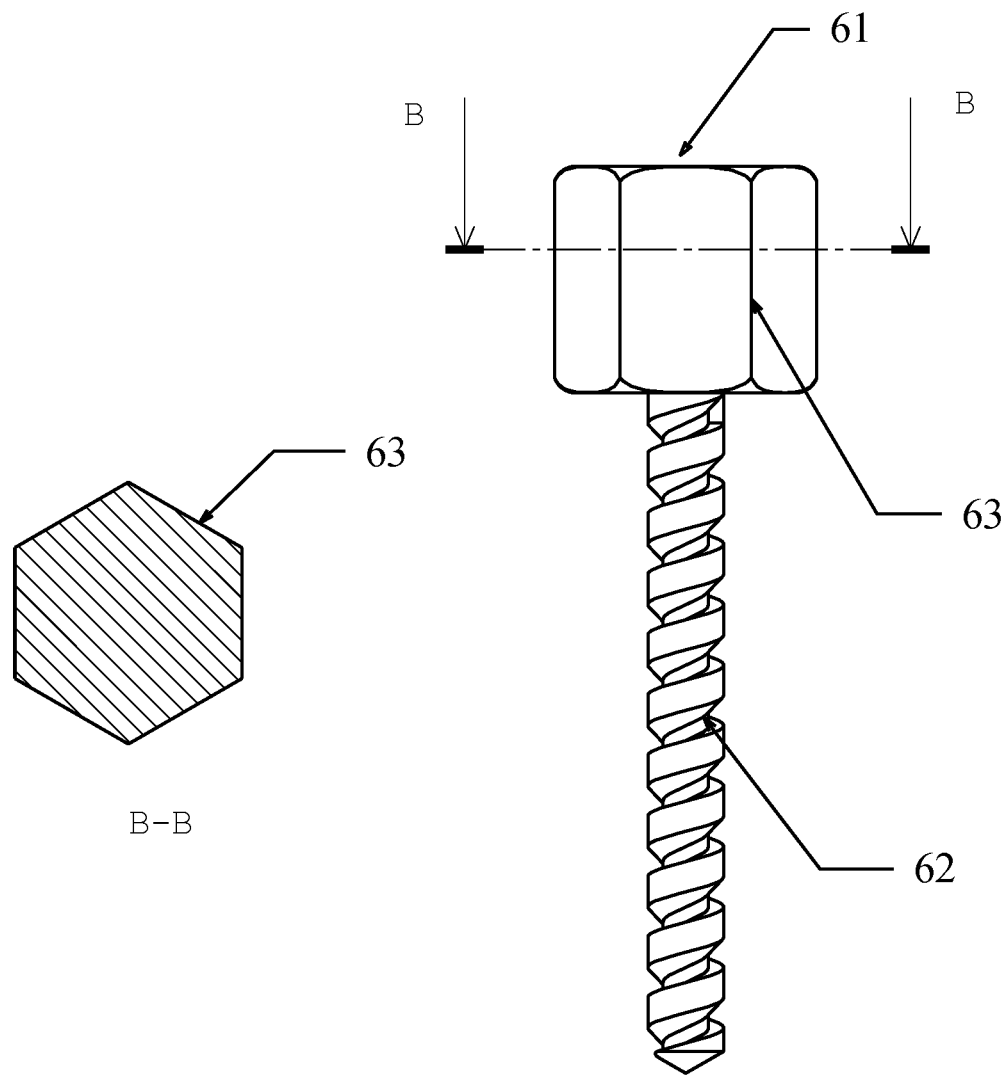
FIG. 10 illustrates a view of a membrane retention screw.

A membrane retention screw is obtained by the method described in Example 1. FIG. 10 shows a front view of the membrane retention screw 61.

The membrane retention screw 61 is in the form of a cylindrical screw of variable length and diameter, has a thread 62 as described in FIG. 6b and is surmounted by a hexagonal head 63 of variable height and diameter. The screw pitch makes it possible to oppose tearing-out when the screw is placed in cortical bone or deficient alveolar bone.

Example 12: Dental Replacement Implant

A dental replacement implant is obtained by the method described in Example 1. FIGS. 11a and 11b show, respectively, a sagittal section and an exploded view of the dental replacement implant 64.

The dental replacement implant 64 comprises a cylindrical body 65 of variable length and diameter, having a thread opposing unscrewing, such as the one described in FIG. 6b. The body 65 is provided, in its upper third, with a ring 66 of Dacron® felt intended to promote fibroblast colonization and producing a genuine gingival setting all round its perimeter, thereby delimiting a gingival attachment zone and a free pseudo-gingiva, opposing migration of the oral fluids and food particles.

This device also has a resilient disk 67, a cap 68, and a pre-prosthetic abutment 69, which elements are made of biocompatible polymer and are intended to receive the prosthetic restoration.

Example 13: Clinical Results

The method of Example 1 is used to prepare 6 T-shaped epiphyseal-diaphyseal plates with 4 open holes, of which the epiphyseal bar measures 15 mm×8 mm×3 mm and of which the diaphyseal bar measures 12 mm×9 mm×3 mm, and fixation screws according to Example 7, of length 33 mm and of diameter 3 mm, which are sterilized by ionizing radiation at 25 KGy in double packaging. These plates are fixed to the outer face of the metaphyseal-epiphyseal region of the tibia of 6 ewes according to a codified surgical protocol.

The animals are anesthetized according to the normal protocol: sodium thiopental (IV) at approximately 1 g/animal, maintenance with isoflurane 1.7-6-1.8% and ketamine prior to the pain phases. After incision of the cutaneous plane and dissection of the musculo-aponeurotic layer and periosteum, the surface of the cortical bone is exposed.

With the aid of a dummy plate provided with drill bushings and placed on the chosen insertion zone, the fixation orifices for the screws of the osteosynthesis material and the locking pins are drilled. After removal of the dummy plate, the fixation orifices are tapped in a manner open from cortical to cortical.

The plate is positioned and maintained in place by support gauges and fixed by the screws by way of the support gauges.

After hemostasis, the deep-lying planes are sutured with resorbable suture threads, the cutaneous plane with non-resorbable threads. The latter are removed after 10 days of cicatrization.

X-rays are taken at D+30 and D+60, and the anatomical pieces are removed at D+60 from three ewes and at D+120 from the other three ewes.

Clinical examination of the anatomical pieces shows that the plates and the screws are perfectly integrated, covered by periosteum.

After translocation, the plates and the head of the screws appear opalescent, imbibed with plasma and adhering to the cortical bone of the bone.

Macroscopic examination shows a modification of the hue of the osteosynthesis plates, and also the presence of a suffusion of amber-yellow liquid, similar to plasma, during sectioning of the plate.

This observation suggests that, during the contact of the plate with the cortical bone and the circulating fluids, the biopolymer layers have been impregnated by these via the interconnected pores of the semi-synthetic hybrid material.

Histomorphometric examination of the interfaces between plate and cortical bone and between screw and endosteum shows an anfractuous lacunary erosion of the inner face of the plate and of the windings of the screws, colonized by osteoblasts, apposition of a subperiosteal metasplasic bone, and significant thickening of the endosteum.

The interface between screw and cortical bone and between screw and medullary cavity shows the same images, namely a lacunary erosion at the surface along the windings of the screws and over the entire length thereof, with apposition of newly formed fresh bone, which suggests that the mesenchymatous strain cells of the bone marrow are the cause of this, with induction of bone-growth-promoting activity.

All of these observations indicate an interactive biological activity between the semi-synthetic hybrid material according to the invention and the receiving bone.

Indeed, it has been demonstrated that the initial presence of osteoclastic giant cells, which are found near the screws in the medullary cavity, are formed by fusion and measure up to 100 µm and derived from the same precursor cells as the monocytes, shows that they are responsible for the formation of crevice-shaped lacunae at the surface of the screws. These crevices can be compared to Howship's lacunae, which are characteristic of osteoclastic activity and indicate bone remodeling. In other words, these observations explain the osteomimetic properties of the plate and of the osteosynthesis screws or implants according to the invention.

All of these features of the semi-synthetic hybrid material of the invention permit an alternative solution to the problems associated with the presence and/or removal of the metallic osteosynthesis material, such as release of toxins, metallosis of the tissues around the prosthesis, systemic effects, weakening of the bone, etc.

This justifies the concept of permanent osteosynthesis material, no longer requiring the removal of the orthopedic material for whatever reason.

The invention claimed is:

1. A semi-synthetic hybrid material, which is the nacreous aragonitic layer of bivalve mollusks selected from the group consisting of *Pinctada maxima, Pinctada margaritifera, Tridacnae maxima, Tridacnae gigas* and other *Pinctada* species, said material comprising an inorganic fraction and a cross-linked organic fraction having cross-linking biopolymer chains formed by cross-linking biopolymer chains with the aid of a cross-linking agent and a physical agent, and said material having a pH from 7 to 7.4.

2. An osteosynthesis device or implant made of semi-synthetic hybrid material as defined in claim 1, which is chosen from osteosynthesis devices such as a straight osteosynthesis plate, an epiphyseal-diaphyseal osteosynthesis plate, an osteosynthesis plate for malleolar fractures, an epiphyseal-diaphyseal osteosynthesis break plate; osteosynthesis screws; membrane retention screws; osteotomy wedges; diabolos; intersomatic wedges and cages; intramedullary nails; humeral and femoral heads; glenoid cavities; tibial plateaus; femoral condyles; vertebral bodies; semi-maxillaries; bones of the ossicular chain; surgical anchors for ligament and/or tendon reinsertion; splints for osteosynthesized reduction of small-fragment comminuted fractures, and dental implants.

3. The device according to claim 2, said device comprises at least one retention means which, during the positioning of said device, opposes the displacement thereof, said retention means being chosen from among a pin, a notch, a keyed and flattened harpoon, a thread against unscrewing.

4. The device according to claim 2, wherein said device further comprises an adjustment element which, during the positioning of said device, permits coaptation thereof.

5. The device according to claim 2, which is an epiphyseal-diaphyseal osteosynthesis break plate and which comprises a break notch.

* * * * *